(12) United States Patent
Kheradvar

(10) Patent No.: US 11,076,952 B2
(45) Date of Patent: Aug. 3, 2021

(54) COLLAPSIBLE ATRIOVENTRICULAR VALVE PROSTHESIS

(71) Applicant: THE REGENTS OF THE UNIVERSITY OF CALIFORNIA, Oakland, CA (US)

(72) Inventor: Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/598,210

(22) Filed: May 17, 2017

(65) Prior Publication Data

US 2017/0252163 A1 Sep. 7, 2017

Related U.S. Application Data

(63) Continuation-in-part of application No. 14/898,048, filed on Dec. 11, 2015, now Pat. No. 9,968,445, (Continued)

(51) Int. Cl.
*A61F 2/24* (2006.01)

(52) U.S. Cl.
CPC .......... *A61F 2/2412* (2013.01); *A61F 2/2418* (2013.01); *A61F 2/2436* (2013.01); (Continued)

(58) Field of Classification Search
CPC .............................. A61F 2/2418; A61F 2/2439
See application file for complete search history.

(56) References Cited

U.S. PATENT DOCUMENTS

| 3,739,402 A | 6/1973 | Cooley et al. |
| 4,259,753 A | 4/1981 | Liotta |

(Continued)

FOREIGN PATENT DOCUMENTS

| WO | WO2013022798 | 2/2013 | |
| WO | WO2013155474 | 10/2013 | |
| WO | WO 2014/201384 | * 12/2014 | ............... A61F 2/24 |

OTHER PUBLICATIONS

International Search Report and the Written Opinion of the International Searching Authority for PCT/US2014/042347; dated Nov. 3, 2014.

(Continued)

*Primary Examiner* — Suba Ganesan
(74) *Attorney, Agent, or Firm* — Tope-Mckay & Associates

(57) ABSTRACT

This disclosure is directed to a collapsible atrioventricular valve prosthesis. The valve includes an annulus wire frame having at least two prongs extending therefrom. At least one catch is formed between each of the prongs and leaflets are attached with the frame, catch, and prongs form the valve. The prongs project a first direction and the catch projects in a direction away from the prongs. The valve is collapsible to provide for easy delivery to an atrioventricular junction or other desired location within a heart. Once deployed, the valve can expand with the catches acting to hold the annulus frame secure on an atrioventricular junction, at a ventricular side or at an atrial side of a heart.

23 Claims, 19 Drawing Sheets

Related U.S. Application Data which is a continuation-in-part of application No. 14/221,194, filed on Mar. 20, 2014.

(60) Provisional application No. 61/835,083, filed on Jun. 14, 2013, provisional application No. 62/337,678, filed on May 17, 2016.

(52) U.S. Cl.
CPC ............... *A61F 2210/0014* (2013.01); *A61F 2220/0008* (2013.01); *A61F 2220/0075* (2013.01); *A61F 2230/0013* (2013.01); *A61F 2230/0095* (2013.01); *A61F 2250/0063* (2013.01)

(56) References Cited

U.S. PATENT DOCUMENTS

| | | |
|---|---|---|
| 5,163,953 A | 11/1992 | Vince |
| 6,309,379 B1 | 10/2001 | Willard |
| 2001/0007956 A1 | 7/2001 | Letac |
| 2001/0039450 A1 | 11/2001 | Pavcnik |
| 2005/0075584 A1* | 4/2005 | Cali ............... A61F 2/2418 600/587 |
| 2005/0101988 A1 | 5/2005 | Stanford et al. |
| 2005/0154442 A1 | 7/2005 | Eidenschink et al. |
| 2007/0016289 A1 | 1/2007 | Johnson |
| 2007/0043431 A1 | 2/2007 | Melsheimer |
| 2007/0100432 A1 | 5/2007 | Case |
| 2007/0203503 A1* | 8/2007 | Salahieh ............ A61B 17/0644 606/108 |
| 2007/0239254 A1 | 10/2007 | Chia |
| 2007/0293935 A1 | 12/2007 | Olsen et al. |
| 2007/0299499 A1 | 12/2007 | Hartley et al. |
| 2008/0039863 A1 | 2/2008 | Keegan et al. |
| 2009/0030497 A1 | 1/2009 | Metcalf et al. |
| 2009/0030512 A1 | 1/2009 | Thielen |
| 2009/0099640 A1 | 4/2009 | Weng |
| 2009/0164003 A1 | 6/2009 | Kheradvar |
| 2009/0192585 A1 | 7/2009 | Bloom et al. |
| 2010/0217382 A1 | 8/2010 | Chau et al. |
| 2011/0040374 A1 | 2/2011 | Goetz et al. |
| 2011/0112622 A1 | 5/2011 | Phan et al. |
| 2011/0196472 A1 | 8/2011 | Sugimoto et al. |
| 2011/0251664 A1 | 10/2011 | Acosta De Acevedo |
| 2011/0319989 A1* | 12/2011 | Lane ............... A61F 2/2418 623/2.11 |
| 2012/0078353 A1 | 3/2012 | Quadri |
| 2012/0165916 A1 | 6/2012 | Jordan |
| 2014/0031924 A1* | 1/2014 | Bruchman ............ A61F 2/2403 623/2.11 |
| 2014/0046433 A1 | 2/2014 | Kovalsky |
| 2014/0214160 A1* | 7/2014 | Naor ............... A61F 2/2418 623/2.36 |
| 2015/0025623 A1* | 1/2015 | Granada ............ A61F 2/2436 623/2.11 |

OTHER PUBLICATIONS

International Preliminary Report on Patentability for PCT/US2014/042347; dated Dec. 23, 2015.
Office Action 1 for U.S. Appl. No. 14/221,194 (non TMA), dated Feb. 4, 2016.
Response to Office Action 1 for U.S. Appl. No. 14/221,194 (non TMA), dated Aug. 2, 2016.
Office Action 2 for U.S. Appl. No. 14/221,194 (non TMA), dated Dec. 30, 2016.
Office Action 1 for U.S. Appl. No. 14/898,048, dated Jan. 17, 2017.
Gupta, et al., "Dimensions of the human adult mitral valve in the embalmed cadaver," J. Morphol. Sci., vol. 30, No. 1, (Mar. 2013), pp. 6-10.

\* cited by examiner

102
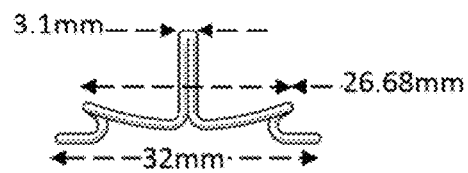
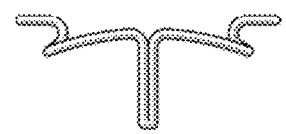
FIG. 4A	FIG. 4B
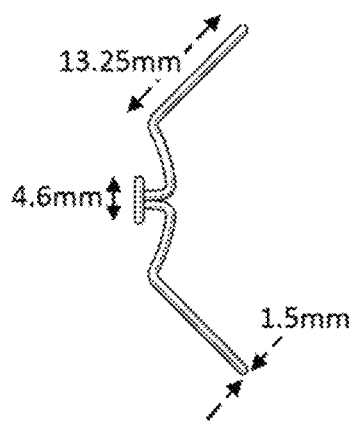
FIG. 4C	FIG. 4D
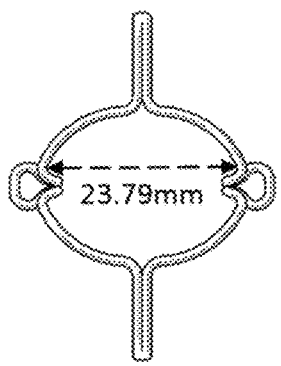
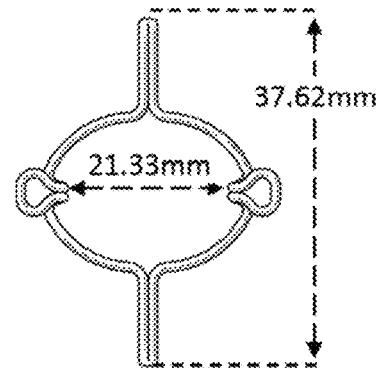
FIG. 4E	FIG. 4F
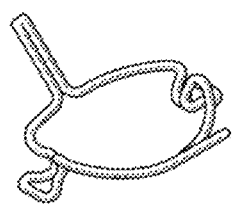
FIG. 4G

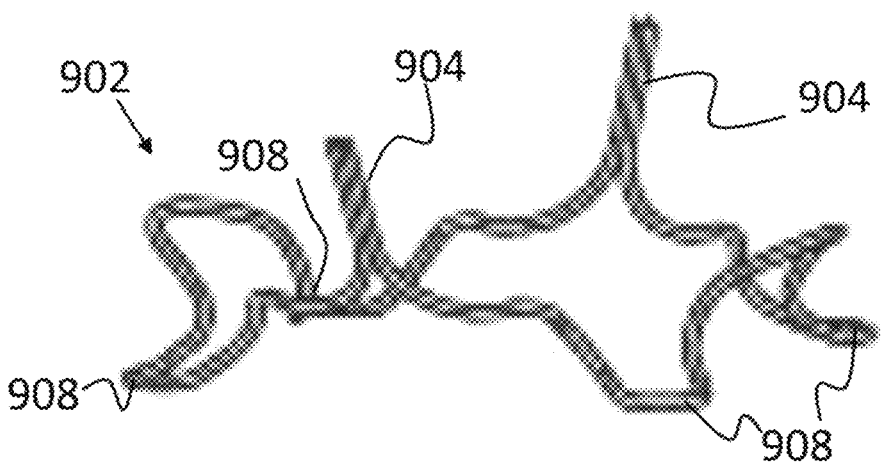
FIG. 11A
FIG. 11C
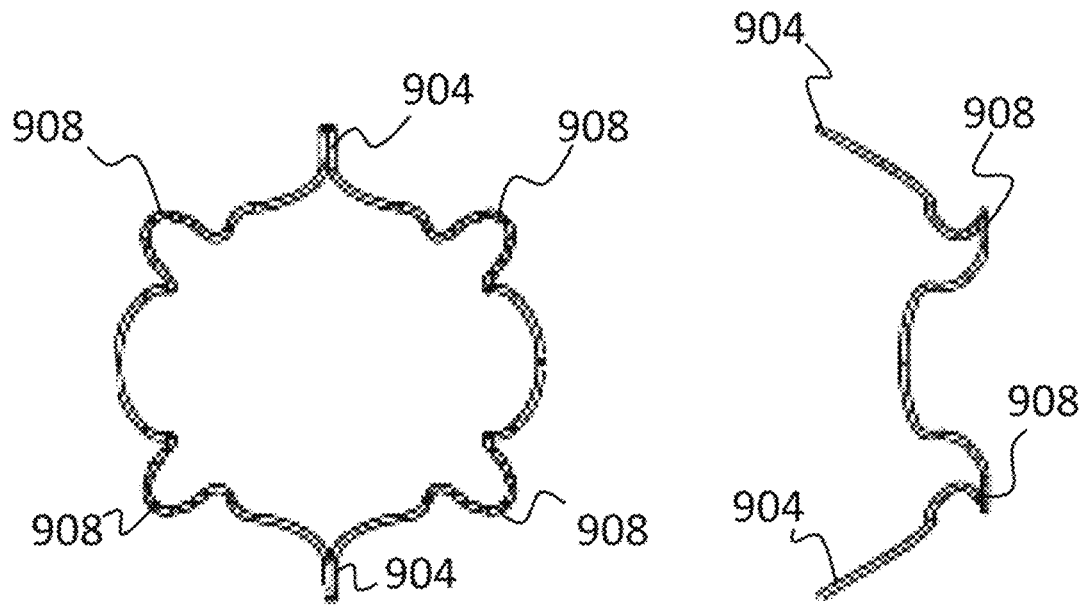
FIG. 11B
FIG. 11D

COLLAPSIBLE ATRIOVENTRICULAR VALVE PROSTHESIS

CROSS-REFERENCE TO RELATED APPLICATIONS

This is a Continuation-in-Part application of U.S. application Ser. No. 14/898,048, filed on Dec. 11, 2015, which is a Continuation-in-Part application of U.S. patent application Ser. No. 14/221,194, filed on Mar. 20, 2014.

U.S. application Ser. No. 14/898,048 is also a non-provisional application of U.S. Provisional Application No. 61/835,083, filed on Jun. 14, 2013.

The present application is ALSO a non-provisional application of U.S. Provisional Application No. 62/337,678, filed May 17, 2016.

BACKGROUND OF THE INVENTION (1) Field of Invention

The present invention relates to a heart valve system and, more particularly, to a collapsible atrioventricular valve prosthesis.

(2) Description of Related Art

Valvular heart disease is the third most common cause of cardiovascular disease in the United States. Mitral Regurgitation (MR) is a common valvular disorder, which can be manifested, in acute and chronic forms. Both the acute and chronic forms of MR are the source of a significant amount of cardiovascular morbidity and mortality. Dysfunction in the mitral valve can arise from abnormalities of any part of the mitral valve apparatus, including the leaflets, annulus, chordae tendineae, and papillary muscles. Additional anatomical support for mitral valve function comes from the left atrial wall and ventricular myocardium adjacent to the papillary muscles. Proper valve function depends on the interaction of all of the anatomic components and a minor dyssynchrony can result in significant valvular dysfunction. With the deranged valvular structure and/or function permitting backflow there is a resultant left ventricular volume overload. Over time and with deterioration of the mitral valve function, this volume overload results in left ventricular dilation and dysfunction. Left ventricular dysfunction in conjunction with MR can lead to pulmonary hypertension, congestive heart failure and ultimately death. Each year in the United States, there are more than 500,000 patients discharged with the diagnosis of MR, and annually in the United States, some 18,000 patients undergo mitral valve surgery. These statistics illustrate the gravity of this problem and the immense cost burden that it creates.

When addressing MR and its etiologies, it must first be identified if the pathologic regurgitation is a result of a primary abnormality of the valve apparatus or secondary to another cardiac disease. When MR is due to a primary abnormality of the valve apparatus, it is referred to as primary MR. The most common causes of primary MR are mitral valve prolapse, rheumatic heart disease and infective endocarditis. Far less common causes of primary MR include trauma and congenital heart disease such as a valve cleft. Secondary MR is most commonly due to ischemic heart disease, left ventricular systolic dysfunction and dilatation (i.e., Functional MR) and least commonly hypertrophic cardiomyopathy. Finally, in the elderly, annular calcification is a cause of MR, however this rarely progresses past moderate and infrequently requires intervention.

Correction of MR within a certain window minimizes the consequences described above. There is a scientifically well-established cause-and-effect relationship between pathologic MR and its deleterious effects on the left ventricle and the patient's life. In the absence of a secondary cause, it is the abnormal valve that makes the heart and thus the patient sick. Definitive therapeutic options for severe MR remain few and the only truly corrective therapies, which require surgical intervention—commonly associated with a median sternotomy—are presently effective. The currently practiced techniques consist of mitral valve repair and replacement. MR is a mechanical problem, thus medical therapy has been shown to be inadequate, and a mechanical intervention (e.g., repair or replacement) is required to improve mortality. Valve competence needs to be restored in order to remove the volume overload and its deleterious consequences. Another controversy within the field of mitral valve repair and replacement is the timing of the intervention.

Currently, decisions are based on a host of factors including symptoms, quantification of left ventricular ejection fraction, age, functional capacity, regurgitant fraction, regurgitant orifice area and regurgitant volume. Imaging and calculation of quantitative measures are performed primarily by Echocardiography. These factors can be subjective and inaccurate. This leads to eligible patients being passed over and perhaps some patients having operations unnecessarily. Finally, a substantial subset of patients is deemed to not be surgical candidates, due to either co-morbid medical illness, age or other factors.

Percutaneous replacement of a heart valve is an incredible development in patient care and one of the great recent breakthroughs in cardiovascular medicine. However, it has been difficult to apply this technology to the mitral valve given its unique anatomical position close to the left ventricular outflow tract. Thus, development of a percutaneous system for mitral valve replacement has not yet been effectively achieved. Development of a percutaneous technology, which has been proven possible in the aortic position would allow for a cure to a very prevalent human disease, while also alleviating a significant amount of suffering associated with both the disease and the current therapeutic options, and finally allowing a more broad range of patients to benefit from the minimally invasive intervention.

The percutaneous approach to valve replacement is a welcome option for many patients due to its sparing of aggressive surgery and reducing the associated comorbidities based on the minimally invasive nature of the procedure. The lure of percutaneous technologies lies in providing cost-effective solutions to heart valve disease, thereby allowing more timely interventions with acceptable efficacy and minimal complications, especially for patients who cannot undergo surgery. These technologies can help avoid open heart surgery in severely ill patients and reduce the number of reoperations in young patients with congenital heart defects.

Nevertheless, there exists numerous challenges in the design and fabrication of a percutanously delivered valves. Thus, a continuing need exists for a well-designed collapsible atrioventricular valve prosthesis that would revolutionize the treatment of valvular heart disease for millions of people.

SUMMARY OF INVENTION

Described is a collapsible atrioventricular valve prosthesis. The valve includes an annulus frame having at least two prongs extending therefrom, and at least two leaflets attached with the frames and prongs to form a valve. In one aspect, the annulus frame is shaped as a saddle or partially-saddle.

In another aspect, the annulus frame further comprises at least one catch that acts to hold the annulus frame secure on an atrioventricular junction or at an atrial or ventricular side of a heart. Thus, in various aspects, the collapsible atrio-ventricular valve is meant to lie between a heart's atrium and ventricular.

In another aspect, the prongs project from the annulus frame in a first direction and the at least one catch projects from the annulus frame in a direction away from the first direction.

In yet another aspect, the annulus frame is symmetric.

In another aspect, the annulus frame is axisymmetric.

In yet another aspect, annulus frame is asymmetric.

In another aspect, each prong is comprised of two wires constrained together by a hypo tube. In various aspect, the hypo tube has a hole that can be used for attachment to a delivery system.

In yet another aspect, the valve is collapsible. The valve is collapsible with a delivery system for percutaneous heart valve delivery.

In another aspect, the annular frame is made of a monolithic wire.

In yet another aspect, the annular frame is formed of a plurality of frame subcomponents.

In yet another aspect, the annular frame is formed of shape-memory material selected from a group consisting of Nitinol, Cobalt-Chromium and polymers.

Additionally, the valve is configurable between a collapsed configuration and an open configuration, such the collapsed configuration allows the valve to be delivered into position against a native atrioventricular valve annulus and upon expanding to the open configuration, the atrioventricular valve is secured in place by the at least one catch.

Further, the leaflets are formed of a material selected from a group consisting of pericardial tissue, polymeric material, and leaflet tissue material.

In another aspect, a surface of the annular frame is rough, thereby accommodating improved sitting at an atrioventricular junction. The annular frame is a wire frame and the surface of the annular frame is rough due to external components added to the wire frame. In another aspect, the annular frame is a wire frame and the surface of the annular frame is rough due to an inherent roughness of the wire frame.

In another aspect, a periphery skin is attached to a circumference of the annular frame, whereby the periphery skirt serves to minimize paravalvular leakage once installed in a patient. The periphery skirt is formed of a material selected from a group consisting of pericardial tissue, polymeric material, and leaflet tissue material.

In another aspect, the valve is collapsible and is deliverable to heart chambers via transapical approach.

In another aspect, the valve is collapsible and is deliverable to heart chambers through peripheral vasculature, comprising transfemoral artery/vein, aorta/vena cava, subclavian vasculature or jugular veins.

Further, the valve is collapsible and is deliverable to heart chambers via surgical procedures comprising, thoracotomy, mini-thoracotomy and minimally invasive heart surgery.

In another aspect, the annulus frame includes three prongs, with at least one catch positioned on the annulus frame between each of the three prongs.

In yet another aspect, the annulus frame includes five catches, such that one catch is positioned on the annulus frame between a first set of adjacent prongs, and two catches are positioned on the annulus frame between a second set of adjacent prongs, and two catches are positioned on the annulus frame between a third set of adjacent prongs.

In another aspect, the annulus frame includes four catches, such that one catch is positioned on the annulus frame between a first set of adjacent prongs, and one catch is positioned on the annulus frame between a second set of adjacent prongs, and two catches are positioned on the annulus frame between a third set of adjacent prongs.

Finally, as can be appreciated by one in the art, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 4A is a bottom-view illustration of a saddle-shaped annulus frame;

FIG. 4B is an top-view illustration of the saddle-shaped annulus frame;

FIG. 4C is a left-view illustration of the saddle-shaped annulus frame;

FIG. 4D is a right-view illustration of the saddle-shaped annulus frame;

FIG. 4E is a front-view illustration of the saddle-shaped annulus frame;

FIG. 4F is a rear-view illustration of the saddle-shaped annulus frame;

FIG. 4G is an isometric-view illustration of the saddle-shaped annulus frame;

FIG. 11A is an isometric-view illustration of a frame of a collapsible atrioventricular valve according to the principles of the present invention;

FIG. 11B is a bottom-view illustration of the frame depicted in FIG. 11A;

FIG. 11C is a front-view illustration of the frame depicted in FIG. 11A;

FIG. 11D is a side-view illustration of the frame depicted in FIG. 11A;

DETAILED DESCRIPTION

Figure 1A:
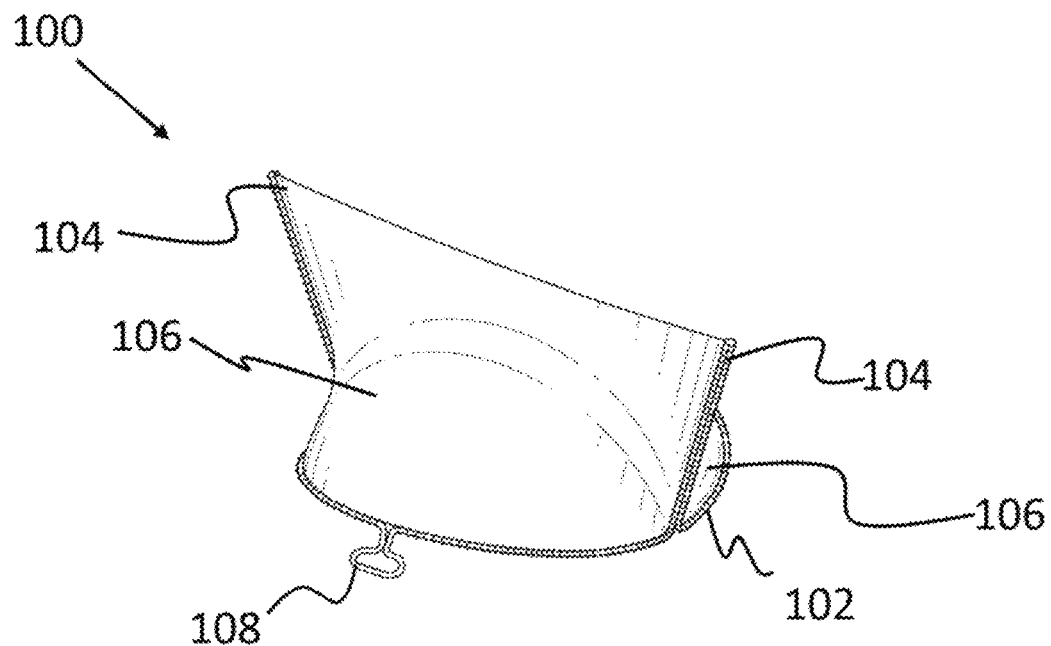
FIG. 1A is an isometric-view illustration of a bioprosthetic mitral valve.
Figure 1B:
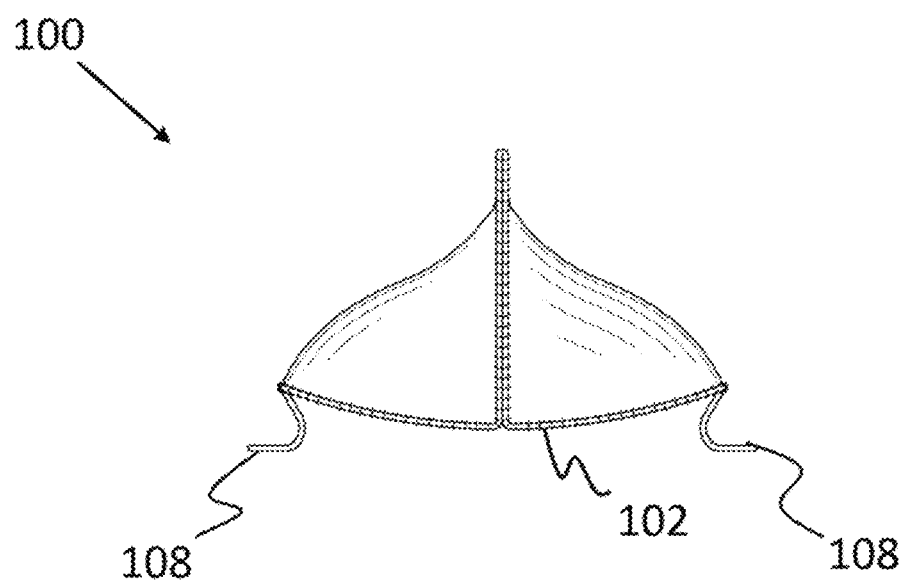
FIG. 1B is a bottom-view illustration of the mitral valve.

The present invention relates to a heart valve system and, more particularly, to a collapsible atrioventricular valve prosthesis. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, rear, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Specific Details

The present invention relates to a collapsible atrioventricular valve prosthesis. Notably, the collapsible atrioventricular valve prosthesis is formed such that it includes an annulus frame (having at least two prongs extending therefrom) and at least two leaflets attached with the frames and prongs to form the valve. Importantly, the present application is directed to a modification of the valve as described in U.S. application Ser. No. 14/898,048 (the '048 application), the entirety of which is incorporated herein by reference. To provide the reader with a complete understanding, FIGS. 1A through 8 are directed to the mitral valve (which is also an atrioventricular valve) as described in the '048 application, while FIGS. 9A through 17 are directed to the collapsible atrioventricular valve prosthesis according to the principles of the present invention. It should be noted that all of the materials, features, functions and operations of the valve as described with respect to FIGS. 1A through 8 can be similarly applied to the collapsible atrioventricular valve prosthesis of the present invention as depicted in FIGS. 9A through 17.

As noted above, the '048 application described a unique percutaneous bi-leaflet mitral valve. The mitral valve can be formed in any desired shape; however and as shown in FIG.

1A, the mitral valve 100 is desirably formed to replicate the natural design of a mitral valve to provide a physiologic advantage in flow and left ventricular function.

The dynamic motion of the natural or native mitral valve is due to the elastic composition of its fibrous annulus. To imitate the motion of the native mitral annulus, an annular frame 102 is formed that is shaped into a saddle-shaped annulus frame with two prongs 104 extending therefrom for attachment of and holding the leaflets 106 (e.g., bi-leaflets). Thus, the leaflets are affixed with the frame 102 and the prongs 104. The frame 102 is formed of any suitably flexible yet stable material, a non-limiting example of which includes super elastic Nitinol wire. Further, the leaflets 106 are formed of any suitably flexible and biocompatible material, non-limiting examples of which include bovine pericardial tissue, leaflet tissue material, and polymeric material, all of any desired width.

As a non-limiting example, the bovine pericardial tissue is approximately 0.5 mm. Thus, in this example, the frame 102 annulus is sutured to the bovine pericardial tissue leaflets 106.

Further, non-limiting examples of the polymeric material include Polysiloxanes, Polytetrafluoroethylene (PTFE) family, polyurethane, and polyvinyl alcohol (PVA). Polysiloxanes are Silicone and Oxygen based polymers. Other non-limiting examples of polymeric materials include Teflon, ePTFE, Gore-Tex®, Dacron based Polyurethanes, including polyester, polyether, polycarbonate, and polysiloxane, J-3 polyurethane (an aliphatic PCU), polyether/PDMS, J-3 polyurethane, Estane (a PEU) and Lycra (a PEUU), and POSS-PCU (polyhedral oligomeric silsesquioxanes-polycarbonate soft segment), a material comprised of interpenetrating networks (IPNs) of Hyaluronan (HA) and Linear Low Density Polyethylene (LLDPE), HA-LLDPE IPNs.

The two leaflets 106 and the saddle-shaped annulus frame 102 are also sutured to each other via the two prongs 104 that extend from the annulus alongside the leaflets 106. The supporting prongs 104 act in similar fashion to the chordae tendineae, preventing the leaflets 106 from being prolapsed toward the atrium.

As will be described in further detail below, the mitral valve 100 can also be formed to include one or more clamps 108 (i.e., a fixture) that extend from the annulus frame 102. As shown in the bottom view of FIG. 1B, the clamps 108 extend from the frame 108 to allow the valve 100 to be compressed for delivery the implantation site (as shown in FIGS. 4A through 4C) and when implanted, assist in affixing the bioprosthetic mitral valve 100 with the annulus of the patients existing and natural mitral valve.

Figure 2A:
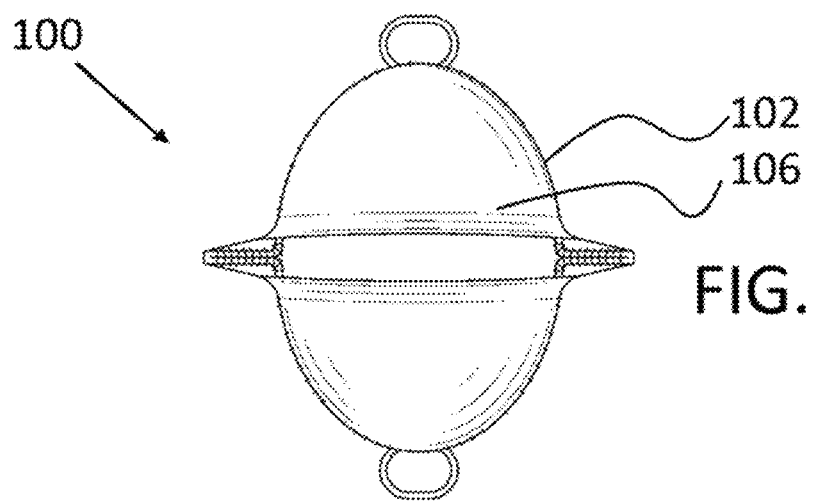
FIG. 2A is a front-view illustration of the mitral valve, depicting the valve as being open.
Figure 2B:
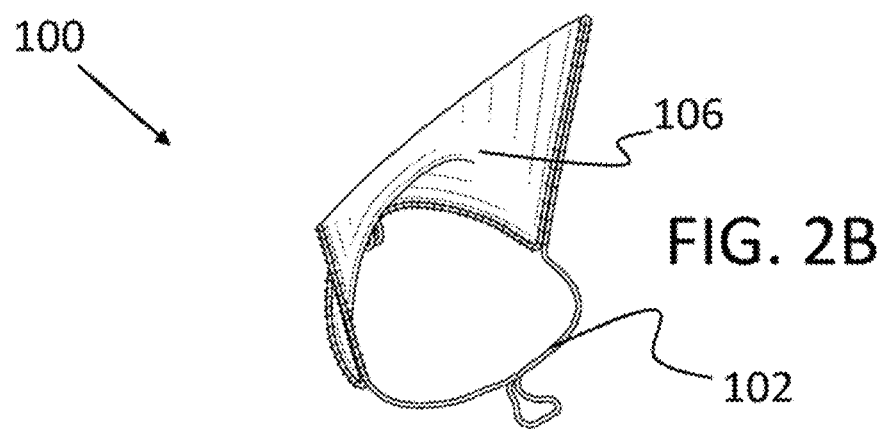
FIG. 2B is an isometric-view illustration of the mitral valve, depicting the valve with foreground leaflets removed for illustrative purposes.
Figure 2C:
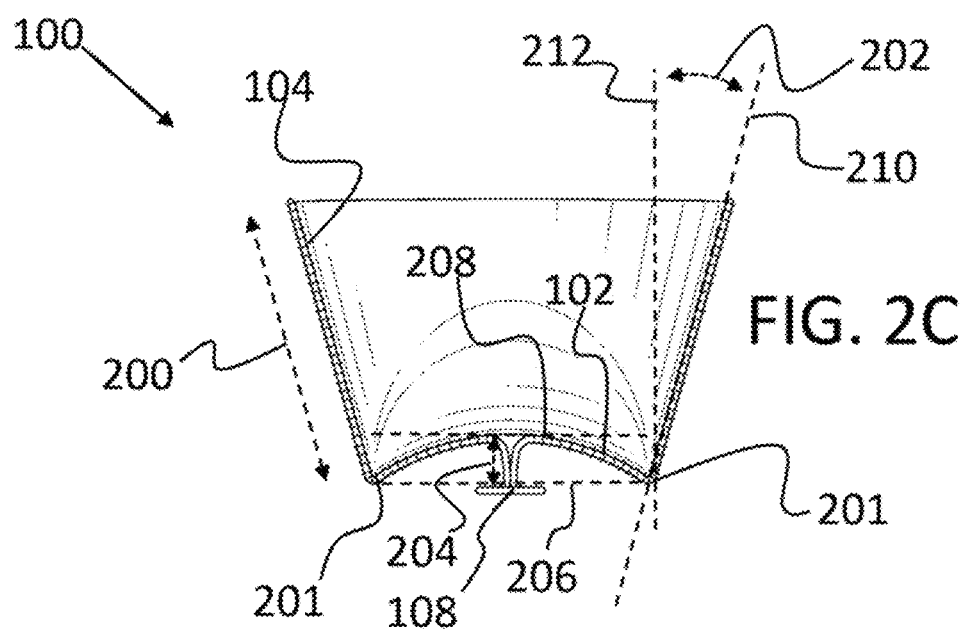
FIG. 2C is a left-view illustration of the mitral valve, depicting the valve with foreground leaflets removed for illustrative purposes.

For further understanding, FIGS. 2A through 2C depict front, isometric, and left views, respectively, of the mitral valve 100. FIG. 2A illustrates the frame 102 and the bi-leaflet 106 design. It should be understood that the valve 100 can be formed of any suitable dimensions to be positioned within a patient's existing natural mitral valve annulus. As a non-limiting example, the mitral valve 100 can be designed for an adult heart with an annulus frame 102 diameter of between 15 and 35 millimeters. In another aspect, the frame 102 diameter is approximately 25 mm (or a radius of 12.5 mm).

As show in the front view of FIG. 2A, the valve 100 is shown as fully open, with the leaflets 106 in an open position to allow blood or fluids to pass therethrough. For further understanding, FIG. 2B shows an isometric-view, depicting a mid-section of the valve (with a front leaflet removed for illustrative purposes). As shown, the Nitinol annulus frame 102 is surrounded by the pericardial tissue (i.e., leaflet 106 material).

The dynamic nature of mitral annulus motion has been verified previously in humans and in animal models. For example, Carlhäll et al. showed that the excursion of the mitral annulus significantly accounted for the total left ventricular filling and emptying in humans (see Carlhäll C, Wigström L, Heiberg E, Karlsson M, Bolger A, Nylander E. Contribution of mitral annular excursion and shape dynamics to total left ventricular volume change. *American Journal of Physiology—Heart and Circulatory Physiology*. 2004; 287:H1836-H1841). This situation arises mainly because the annulus plays a sphincter-like role when facilitating ventricular filling and valve closure during diastole and systole, respectively. In addition, the geometry of the mitral annulus has been shown to be a significant parameter in the diagnosis of functional disorders such as mitral valve prolapse, functional mitral regurgitation and acute ischemic mitral regurgitation. The mitral valve is a major contributor of the ventricular flow pattern, which is extremely critical with respect to momentum transfer, energy dissipation and the pumping efficiency of the left ventricle. Thus proper design of the Nitinol saddle annulus for the valve is critical to maintaining a novel and bio-inspired approach to create the first bioprosthetic mitral valve that mimics native physiology.

For further understanding, FIG. 2C is a left view of the image shown in FIG. 2B, depicting the valve 100 in an open configuration. Of particular note is the prong length 200, prong angle 202, and annulus rise 204. The prong length 200 is the length of the prong 104 as it rises from an intersection 201 of the frame 102. The prong length 200 is formed at any desired length. Desirably, the prong length 200 is sufficiently long to allow the annulus frame 102 to rest against the annulus of the native mitral valve, while extending from the intersection 201 to a length that allows the leaflet 106 to cover (or support) an existing native mitral valve leaflet. As a non-limiting example, the prong length 200 is between 5 and 30 mm. In another aspect, the prong length 200 is desirably approximately 11 mm or 25 mm. For example, if approximately 11 mm, then the valve 100 would be considered a short leaflet valve. Alternatively, if approximately 25 mm, then the valve 100 would be considered a long leaflet valve.

The annulus rise 204 is a measurement that reflects the curvature of the saddle-shaped annulus frame 102. In other words, the annulus rise 204 is the distance between a line 206 that crosses the bottom most portion of the frame 102 (illustrated at the intersection 201) and a line 208 that crosses an apex of the curvature. The annulus rise 204 is any desired distance that operates to maximize flow and valve 100 function and that assists the valve 100 in maintaining affixation with a native mitral valve. Further, the annulus rise 204 assists in positioning the clamps 108 such that they operate effectively to clamp the valve 100 against the native mitral valve annulus. As a non-limiting example, the annulus rise 204 is between 2 and 5 mm. As another non-limiting example, the annulus rise 204 is approximately 3.25 mm.

The prong angle 202 is the angle between a prong axis 210 and a vertical axis 212 rising vertically from an intersection 201 (i.e., the point at which the prong axis 210 begin). The prong angle 202 is any suitable angle that operates to maximize flow and valve 100 function and that assists the valve 100 in maintaining affixation with a native mitral valve. As a non-limiting example, the prong angel 202 is between 5 and 40 degrees. In another aspect and as another non-limiting example, the prong angle 202 is approximately 20.2 degrees.

The mitral valve 100 has been designed to exhibit optimal fluid dynamics with minimal stress development over the leaflets 106. To understand the effectiveness of a traditional bi-leaflet valve, a study was conducted to examine the effect of a dynamic saddle annulus on transmittal flow and stress distribution among the leaflets.

To begin the analysis of a traditional bi-leaflet valve, the stress distribution over the valve leaflets was computationally modeled. The solid geometry of the Nitinol framework and the leaflets were independently developed and imported into a computational analysis software environment. CATIA (by Dassault Systémes Americas Corp., located at 175 Wyman Street, Waltham, Mass. 02451, USA) and ABAQUS (by SIMULIA, a division of Dassault Systémes Americas Corp.) were utilized for mechanical design and computational analysis, respectively. Additionally, an in vitro hemodynamic study was undertaken using a heart-pulsed flow duplicator. Transmitral vortex formation was also studied using the same system, for several different sizes of the valve to determine which one replicates the native mitral valve flow the best.

The results of the study were compelling in demonstrating that bi-leaflet valves, regardless of their leaflets' height, produced a more physiologic transmitral vortex and a more favorable stress distribution when compared to the standard tri-leaflet bioprostheses. In normal hearts, the leading vortex of the native asymmetric transmitral vortex transfers extra momentum from the left atrium to the left ventricle, thus contributing to an efficient transport of blood towards the aorta. The additional sources of momentum-transfer derive either from the added mass effect, in which the streamlines act as a boundary that drives the ambient fluid into motion when the vortex is being formed, or from fluid entrainment inside the isolated transmitral vortex bubble. The proximity of the leaflet tips to the ventricular wall will significantly affect the process of vortex formation, and the flow pattern observed downstream of the bileaflet prototype that generates an asymmetric vortex may be closer to reality as shown before. Additionally, a major concern with any bioprostheic heart valve is durability. Minimizing the stress on the leaflets and distributing it more evenly is critical to maintaining functionality and durability of the valve.

Figure 3:
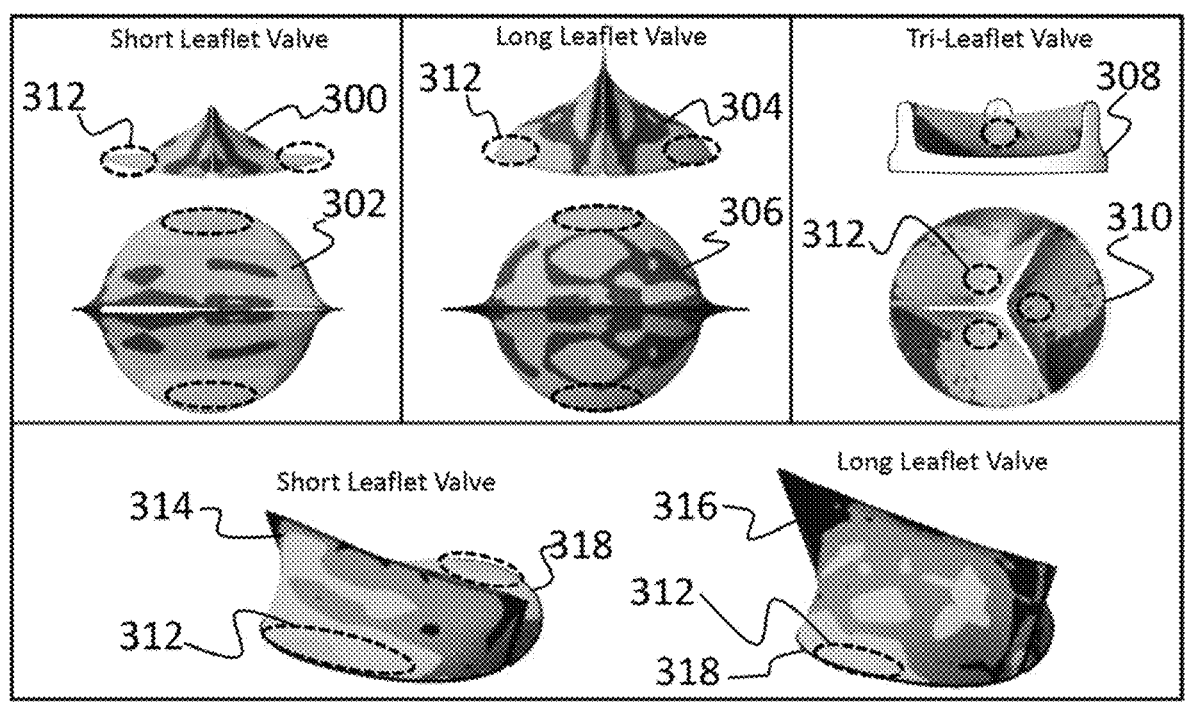
FIG. 3 is an illustration depicting stress test results of a short and long bi-leaflet type valve, as contrasted with tri-leaflet type valve.

As illustrated in FIG. 3, using a Von Mises stress distribution, it was shown that stress distribution over the leaflets in a bi-leaflet type valve during valve closure was more even and reduced in a bi-leaflet valve with a dynamic annulus when compared to standard tri-leaflet valve with rigid annulus. In a bi-leaflet type valve, more of the stress was transferred to the annulus which improves durability. Specifically, FIG. 3, illustrates testing results of two versions of a bi-leaflet type valve (i.e., short leaflet valve and long leaflet valve). Depicted at the top of FIG. 3 are a bottom view 300 and front view 302 of the stress distribution over the leaflets of a short leaflet bi-leaflet valve. Also depicted are a bottom view 304 and front view 306 of the stress distribution over the leaflets of long leaflet bi-leaflet type valve. The short and long bi-leaflet type valves are to be contrasted with the stress distributions of a traditional tri-leaflet valve, shown in the bottom 308 and front 310 views, respectively. The lighter areas in the images illustrate higher stress regions or points, with the areas of greatest stress 312 for each design being circled with a dashed line. As clearly illustrated in the isometric views of the short leaflet bi-leaflet type valve 314 and long leaflet bi-leaflet type valve 316, higher concentrations of stress is developed over the saddle-shape annulus 318 compared to the leaflets in the bi-leaflet type valves.

Thus, as described above and illustrated, the bi-leaflet design is more favorable with regard to left ventricular hemodynamics and stress on the bioprosthetic leaflets. Given the previous research briefly described above, it affirms advantages of the transcatheter bi-leaflet mitral valve for transapical implantation. To assist in transcatheter delivery, the valve 100 must be collapsible and formed in a catheter based design.

To form the frame 102, a mold can be used that mimics the saddle shape annulus of the native mitral valve. The mold is formed of either aluminum or stainless steel (or any other suitable material) based on the temperature of the furnace that is used for heat treatment, which is determined in conjunction with a machinist skilled in the art. CATIA design software is used for part design, and fabrication of the mold can be easily accomplished using a hired machinist that is skilled in the art, such as those commonly employed by the University of California Irvine, in Irvine, Calif., USA. The mold is used to mount the frame material for heat treatment. As a non-limiting example, the mold is used to mount the Nitinol wires for heat treatment.

Nitinol alloys are materials that have two very unique properties: shape memory and superelasticity. Shape memory refers to the ability of Nitinol to deform at one temperature, and then recover its original, undeformed shape upon heating above its "transformation temperature". Superelasticity occurs at a narrow temperature range just above its transformation temperature; in this case, no heating is necessary to cause the undeformed shape to recover. Nitinol exhibits enormous elasticity, some 10-30 times that of ordinary metal. Thus, Nitinol is used in this design (as a non-limiting example of a suitable frame material) to provide a collapsible frame for the valve. Once the mold is formed mimic the saddle shape of the native mitral valve annulus, the Nitinol is heat treated in the mold to generate a new resting shape of the valve annulus frame.

Non-limiting examples of a suitable annulus frame 102 are illustrated in FIGS. 4A through 4G, which illustrate a bottom view, a top view, a left view, a right view, a front view, a rear view, and an isometric view, respectively, of the frame 102. It should be noted that the specific dimensions illustrated in FIGS. 4A through 4G are provided for illustrative purposes of a single non-limiting example of suitable dimensions. Importantly, it is to be expressly understood that the present invention is not intended to be limited thereto and that the illustrated dimensions are provided as but one non-limiting example of such suitable dimensions. As noted above, valve characteristics, such as annulus height (i.e., prong length), curvature (i.e., annulus rise) and the critical prong angle, are optimized by constraining the Nitinol wire to a specialized mold designed for an adult heart with an annulus diameter of approximately 25 mm (or any other suitable dimension as described above).

In one aspect, once the Nitinol annulus frame 102 has been formed it will be fused to two Nitinol supporting prongs 104 that extend from the annulus frame 102 alongside the leaflets 106. The supporting prongs 104 can be formed or fused to the frame using any suitable formation or fixation technique, non-limiting examples of which include being wielded to the frame 102, being press fit within a tiny tube, or both, or any other suitable technique.

The supporting prongs 104 act in similar fashion to the chordae tendineae, preventing the leaflets from being prolapsed toward the atrium. All Nitinol components of the valve 100 will share super-elastic properties and thus be amenable to the deformation required to fit into the delivery system. Proper design and optimal spread of these prongs 104 are critical, as the bovine pericardial leaflets 106 will ultimately be sutured to the prongs 104.

A fabric or sheet material can optionally be used to enclose the Nitinol annulus frame 102 and prongs 104. As a non-limiting example, a polyester stretch fabric, which is commercially available from Bard Medical (located at 8195 Industrial Boulevard, Covington, Ga. 30014, USA), can be used to enclose the Nitinol annulus frame 102 and support prongs 104. This fabric serves the purpose of creating a surface which the pericardial leaflets 106 can be sewn to, and providing the annular frame 102 with a surface or substrate that will induce a more rapid overgrowth by the endothelium. The sooner the percutaneously placed valve 100 has its annulus frame 102 covered by endothelium, the more stable the bioprosthesis will be. Finally, the pericardial leaflets 106 will be sutured to the prongs 104 and/or frame 102. Once the leaflets 106 are secure, the mechanical assembly of the valve 100 will be complete and the valve 100 can be implanted within the patient through percutaneous transcatheter delivery. It should be noted that in one aspect, the fabric or sheet is used and attached to the frame 102 and prongs 104. In another aspect, the leaflets 106 are attached directly to the frame 102 and prongs 104 without the inclusion of such a fabric or sheet.

Figures 5A, 5B, 5C:
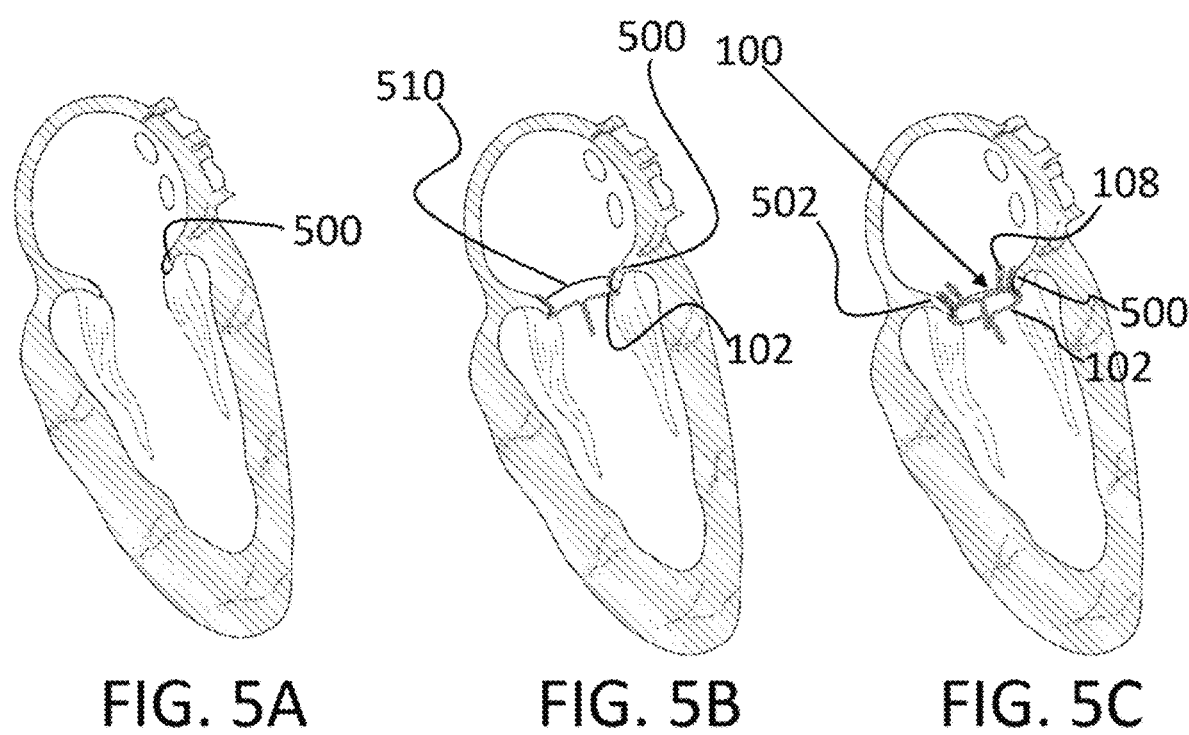
FIG. 5A is an interior-view illustration of a heart chamber, depicting a native mitral valve annulus.
FIG. 5B is an interior-view illustration of the heart chamber, depicting a bioprosthetic mitral valve as attached with a native mitral valve.
FIG. 5C is an interior-view illustration of the heart chamber, depicting a bioprosthetic mitral valve as attached with a native mitral valve.

To achieve stability and fixation in the mitral valve annulus, the valve frame 102 can be formed to include a sub-annular fixture. The sub-annular fixture is any suitable mechanism or device that assists the valve 100 in securely attaching to the patient's existing mitral valve annulus. Two non-limiting examples of such a fixture are described below. For example, the annulus frame 102 can machined to include one more Nitinol clamps 108 (e.g., between two to ten; however, desirably, two) that are machined into the frame 102. In this example and as shown in FIG. 5C, the Nitinol clamps 108 will be evenly distributed below the annulus 102, which upon valve expansion, the Nitinol annulus 102 would be triggered to spring closed and grasp the native valve annulus 500 between the clamp 108 and the Nitinol annulus frame 102. For further understanding, FIG. 5A is an interior view of a heart chamber, depicting a native mitral valve annulus 500. FIG. 5C is an interior view of the heart chamber, showing the Nitinol clamps 108 as extending radially from the annulus frame 102 of the mitral valve 100 to grab the heart tissue 502 and fix the valve 100 in place against the native mitral valve. Note that the valve leaflets are removed for illustrative purposes.

Another example of a design for the fixture is illustrated in FIG. 5B and includes a second Nitinol annular ring 510, which would sit below the first (i.e., the annular frame 102), allowing the capture of the native annulus 500 between the two rings 510 and 102. In other words, in this aspect, the valve is a dual ring version that includes two rings (i.e., frame 102 and ring 510) that are connected with one another, with one sitting on the atrial side and the other on the ventricular side of the annulus 500 and press the annulus 500 between them. Although not strictly required, in one aspect, it is desirable for the second Nitinol annular ring 510 to be slightly thinner and more collapsed in the delivery catheter than the first ring (i.e., the annular frame 102).

A reduction in collapsed size is critical when designing a percutaneous heart valve, as the smaller the collapsed configuration, the lower profile the delivery system can be, whether that is transapical or transfemoral. The super-elastic properties of Nitinol will allow for the valve to be deformed fitting the design of the catheter. When the profile or French size of the delivery system is minimized, then the myocardial injury, in the case of transapical, or vascular injury in the case of trans-femoral, can be minimized.

Figure 6A:
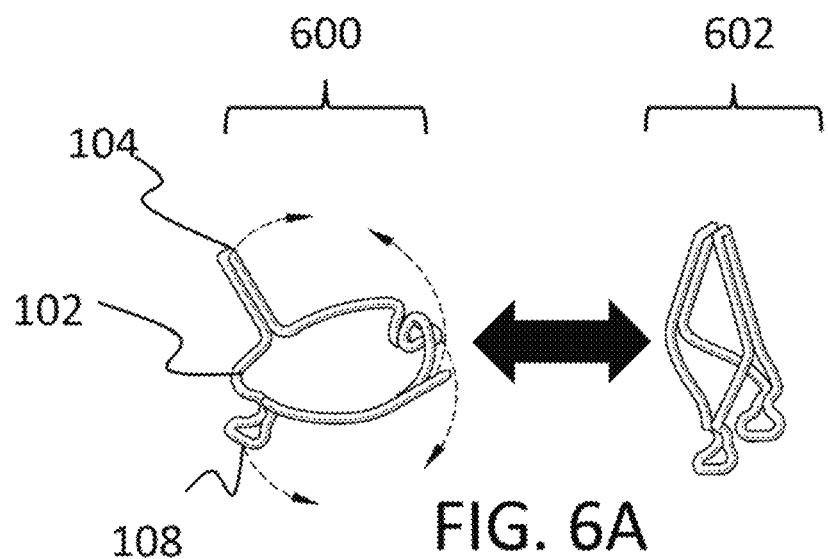
FIG. 6A an isometric view illustration of the saddle-shaped annulus frame, depicting the frame as changing between an open and collapsed configuration.
Figure 6B:
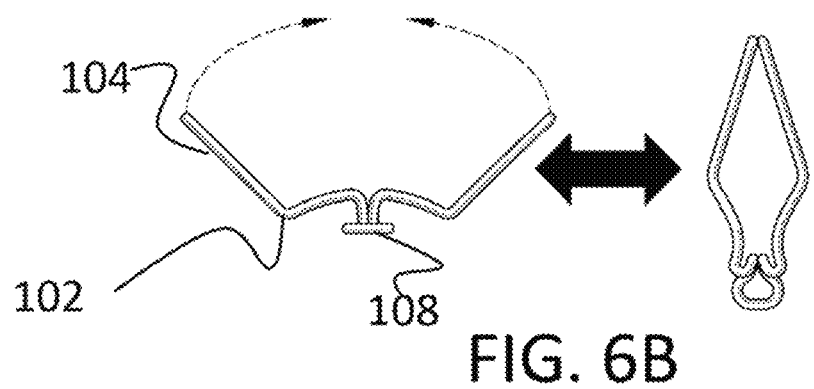
FIG. 6B a side-view illustration of the saddle-shaped annulus frame, depicting the frame as changing between an open and collapsed configuration.
Figure 6C:
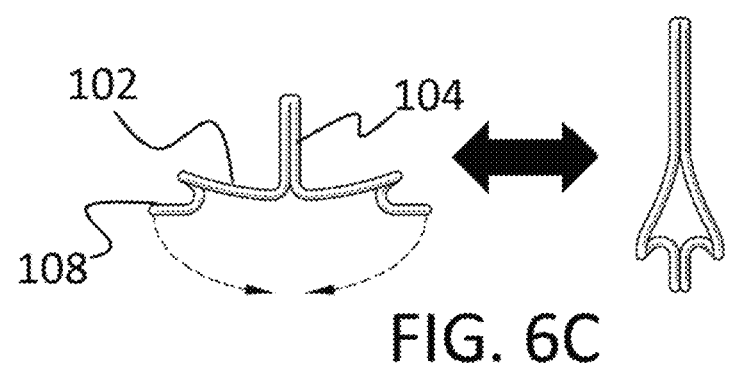
FIG. 6C a front-view illustration of the saddle-shaped annulus frame, depicting the frame as changing between an open and collapsed configuration.

For example, FIGS. 6A, 6B, and 6C illustrate isometric, side, and front views, respectively, of the annular frame 102. Specifically, the figures depict the annular frame 102 as folding between an open configuration 600 and a collapsed configuration 602. Also as shown, the frame 102 is moved into the collapsed configuration 602 by pressing the clamps 108 toward one another and the prongs 104 toward one another. Because the Nitinol annular frame 102 is shape set into the open configuration 600, once delivered to the appropriate place and released, the annular frame 102 will automatically revert from the collapsed 602 to open configuration 600, thereby affixing the valve in place against the native mitral annulus.

Thus and as mentioned above, described is also a delivery system that could facilitate transapical implantation or transfemoral or direct aortic delivery routes to the mitral valve that delivers the mitral valve in the collapsed configuration 602 and once released, allows the mitral valve to revert to the open configuration 600 and become affixed with the native mitral valve. It should be understood that the specific delivery catheter as described and illustrated is provided as a non-limiting example of such a delivery system and that any other suitable mitral valve delivery system can be employed to implant the mitral valve against the native mitral annulus.

For example, the design is for a transapical delivery system to optimize the repositionability of the valve due to the anatomic position for the mitral valve. The catheter is minimized in size to provide the lowest diameter possible to minimize apical injury on implantation and bleeding risk once the catheter is removed. As a non-limiting example, the catheter has a diameter in range of 12 Fr to 32 Fr.

As noted above, the catheter is directed to the transapical approach. There are several advantages to this approach. To begin with, the anatomical position of the mitral valve makes a transfemoral approach much more complicated than it is for the aortic valve. Accessing the mitral valve from a transfemoral approach requires either a venous approach with a puncture through the intra-atrial septum, or an approach through the aortic valve initially then retrograde through the mitral. Both vascular approaches have major drawbacks and complications. For instance, as with all procedures involving percutaneous vascular access, the risks of bleeding and major vascular injury are significant. Additionally, a transapical catheter allows a larger internal diameter than a transfemoral catheter. With a transapical approach, there is a cardiothoracic surgeon present and the risks of bleeding are less. Additionally there are less common complications such as persistent shunt that occurs after transseptal puncture, left ventricular injury and malignant arrhythmia when taking a retrograde approach. Therefore, due to the advantages discussed above, the catheter is devised for the transapical approach for mitral valve implantation. Goals of the catheter are: (1) A low profile, to enhance access and improve closure (2) Hemostatic control to minimize blood loss during insertion, and (3) Minimal left ventricular trauma during insertion.

Figure 7A:
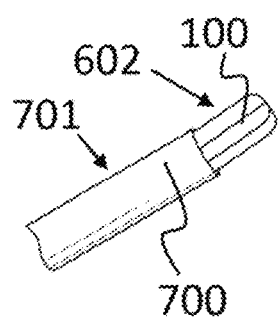
FIG. 7A is an illustration of a delivery catheter, depicting the mitral valve as starting to protrude from the delivery catheter.
Figure 7B:
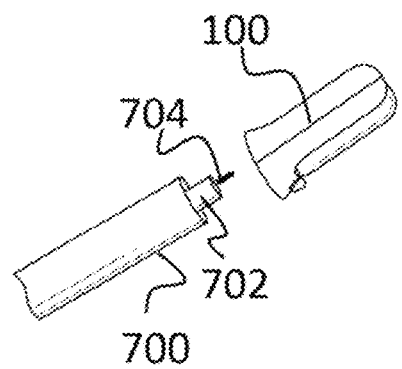
FIG. 7B is an illustration of a delivery catheter, depicting the mitral valve as removed from the delivery catheter.
Figure 7C:
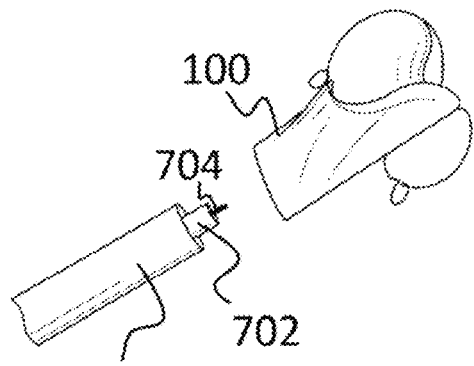
FIG. 7C is an illustration of a delivery catheter, depicting the mitral valve as expanding from the collapsed to the open configuration.
Figure 7D:
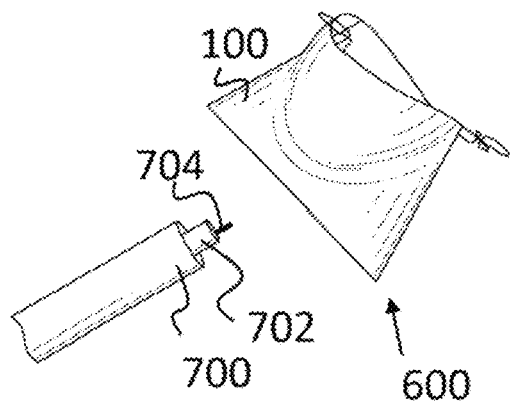
FIG. 7D is an illustration of a delivery catheter, depicting the mitral valve in the open configuration.

Currently there are several transapical delivery systems for the various transcatheter aortic valves. These systems consist mainly of a main delivery catheter, an external delivery control system and a balloon lumen for those valves that are balloon expandable. As applied to the mitral valve and as show in FIGS. 7A through 7D, there is no balloon lumen to deal with as using the superelastic properties of Nitinol results in a self-expanding valve 100 that transforms from the collapsed configuration 602 to the open configuration 600 when released from the delivery catheter. Specifically, FIG. 7A illustrates an example schematic of a first stage of transapical valve delivery where the valve 100 is starting to protrude from the delivery catheter 701 (and its sheath 700). FIG. 7B illustrates the still crimped valve 100 once it has been removed from the delivery catheter for positioning, while FIG. 7C illustrates a partially unfolded valve 100. Finally, FIG. 7D illustrates a fully unfolded valve in the open configuration 600. Notably, in FIGS. 7C and 7D, posterior leaflets are removed for illustrative purposes.

As noted above and as shown in FIGS. 7A through 7D, the delivery catheter 701 includes a sheath 700 with a size on the order of 25-30 French (or any other suitable size), which is consistent with the sizing dimensions commercially available today in the United States and Europe. This catheter is designed with a corresponding dilator with a central lumen 702 for a rigid wire 704 that will be inserted to start the delivery process. The catheter 701 and sheath 700 design are well-developed technologies that are clearly understood by those skilled in the art.

In this case, the valve 100 is crimped (into the collapsed configuration 602) and positioned in the sheath 700. When in the desired location, the rigid wire 704 is pushed to force the valve 100 from the sheath 700 to engage with and attach with the native mitral annulus.

It should be noted that in addition to the sheath 700 design, the catheter 701 includes an external delivery and control system (i.e., handle). This system will consist of a one handed control that will allow the operator four degrees-of-freedom, with movement in the x, y and z planes, along with rotation along the axis of the sheath 700. Once the valve 100 is in optimal position, the device will allow the operator to partially deploy the valve to ensure optimal position under Fluoroscopy and 3-Dimensional Transesophageal Echocardiography. Such a catheter and delivery and control system is described in U.S. patent application Ser. No. 14/221,194, entitled, "Percutaneous Heart Valve Delivery Systems," filed on Mar. 20, 2014, which is hereby incorporated by reference as though fully set forth herein.

Based on this concept, if the valve is not in optimal position, the delivery and control system will allow for re-sheathing of the valve 100 and the ability to re-deploy in an alternate location. After an optimal position has been obtained, the system will release the valve and it will secure itself in place. Another advantage to the transapical system is the decreased complexity in movement of the delivery and control system.

Figure 8:
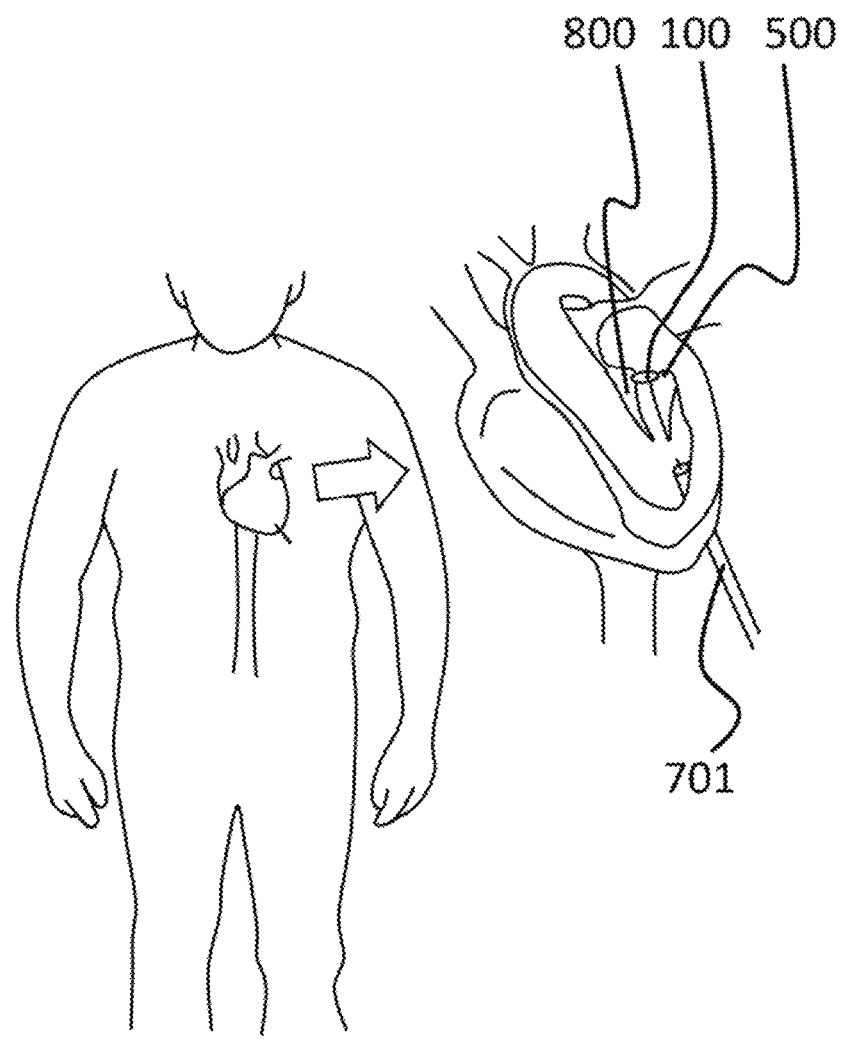
FIG. 8 is an illustration depicting an anatomical approach taken during a transapical mitral valve replacement.

For further illustration, FIG. 8 provides an illustration depicting the anatomical approach taken during a transapical mitral valve replacement. As shown, the catheter 701 is used for transapical implantation of the bioprosthetic mitral valve (or the valve of the present invention). Specifically, the catheter 701 is used to position the bioprosthetic mitral valve 100 in place against the patient's native mitral valve 800 and its corresponding native valve annulus 500 (as depicted in FIGS. 5B and 5C).

Thus, the mitral valve 100 is to be positioned into an existing human mitral valve 800 (i.e., the native mitral valve) and left in place to support the existing native mitral valve. In one aspect, the mitral valve 100 is simply left in place to support the existing native mitral valve 800. In another non-limiting aspect, after being positioned into place, the mitral valve 100 can be further affixed with the existing native mitral valve 800 using any fixation technique. As a non-limiting example, the bioprosthetic mitral valve 100 can sewn or hooked against the native mitral valve 800. For example, the leaflets of the bioprosthetic mitral valve 100 can be sewn against the native mitral valve 800 leaflets. As another non-limiting example, the saddle-shaped frame of the bioprosthetic mitral valve 100 can be sewn against the native valve annulus 500. Such a process can be accomplished using any suitable mechanism or device that is operable for in vivo fixation or stitching. As a non-limiting example, NeoChord, Inc. (located at 7700 Equitable Drive, Suite 206, Eden Prairie, Minn. 55344, USA) has developed a device for mitral valve repair that repairs, in vivo, torn leaflets with sutures. The Neochord mitral valve repair device can be employed to stitch the frame 102 against the native valve annulus 500 and/or the leaflets 106 against the native mitral valve leaflets. Thus, in this aspect, the Neochord device, instead of sewing a torn leaflet, is used to suture the mitral valve 100 in place against the native mitral valve 800.

As noted above, all of the materials and features as applicable to the mitral valve (which is a bicuspid atrioventricular valve) as described above and in the '048 application) are similarly applicable to the collapsible atrioventricular valve prosthesis according to the principles of the present application and as described in further detail below. While the mitral valve as depicted in FIGS. 1a through 8 depicts only two prongs and two catches clamps) as a non-limiting example, the present invention is not intended to be limited thereto and can have any desired number of prongs and catches (clamps) in any desired configuration.

As a non-limiting example, FIGS. 9A through 9E depict an isometric-view, a top-view, a bottom-view, a front-view, and a side-view, respectively, of the collapsible atrioventricular valve prosthesis 900 according to the principles of the present invention. As shown in FIGS. 9A through 9E, the collapsible atrioventricular valve prosthesis 900 is formed of an annulus frame 902, having at least two prongs 904 (or more) extending therefrom. At least two leaflets 906 (or more) are attached with the frames 902 and prongs 904 to form the valve 900.

In the actual example depicted, the valve prosthesis 900 has three prongs 904. Leaflets 906 are affixed with the frame 902 and/or prongs 904 to form the valve prosthesis 900, which in this case is a tricuspid valve 900. An advantage to this configuration is that it is a tricuspid valve (as opposed to the bicuspid valve of FIG. 1) which is often more commercially desirable and can in many cases be more stable or less prone to failure. Further, while the mitral valve is a bicuspid atrioventricular valve, the other atrioventricular valve is a tricuspid valve. In the native heart, the natural tricuspid valve is between the right atrium and the right ventricular. While the valve 900 of the present invention can be deployed in such a location, it should be noted that the present invention is not intended to be limited thereto as it can be deployed in any desired location within a native heart or other suitable location.

Notably, between each prong 904 there is at least one catch 908 formed on the frame 904 that protrudes downward from the frame 902 (when the prongs 904 project upward), forming an axisymmetric-shaped frame 904. The catch 908 is an appendix or fixture that is shaped (e.g., includes a hook-shaped or curvature) to act as a catch or clamp to hold the valve frame 902 secure on the atrioventricular junction or at the atrial side of the heart when installed and deployed. The catch 908 is similar to the clamp as described above with respect to FIGS. 1A through 8. It is noted that in some embodiments the catches 908 protrude away from the frame 902 in a direction generally opposite that of the prongs 904.

Figure 9A:
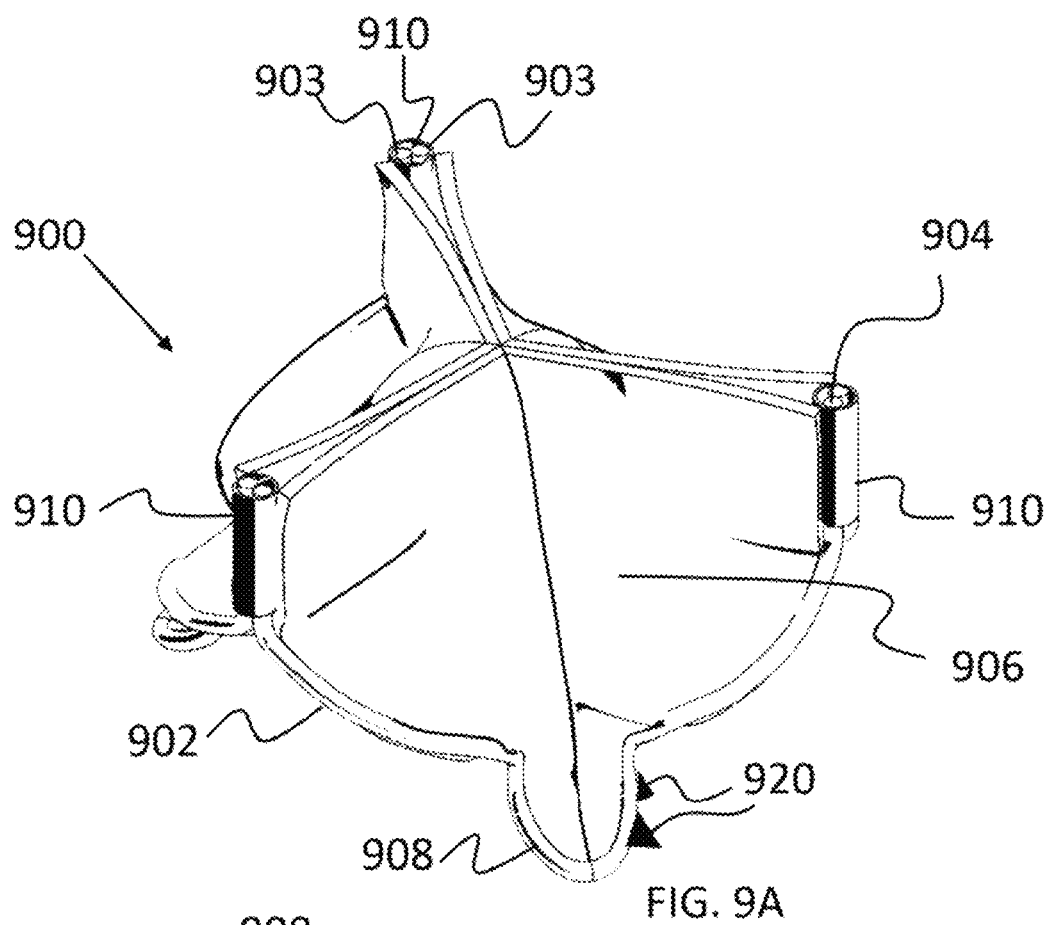
FIG. 9A is an isometric-view illustration of a collapsible atrioventricular valve prosthesis according to the principles of the present invention.
Figure 9B:
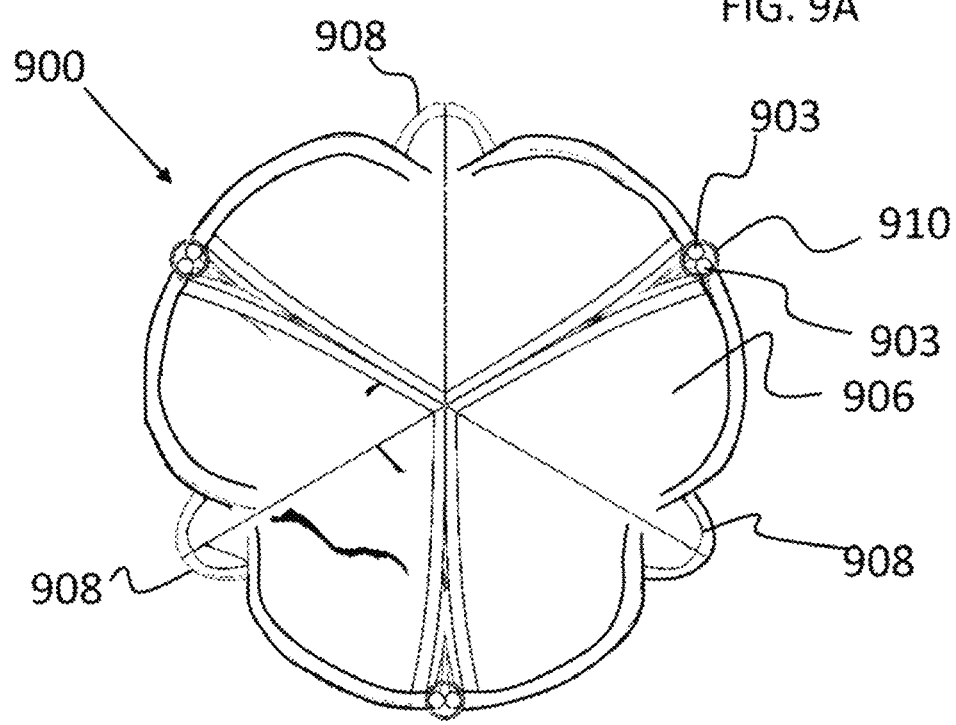
FIG. 9B is a top-view illustration of the collapsible atrioventricular valve prosthesis according to the principles of the present invention.
Figure 9C:
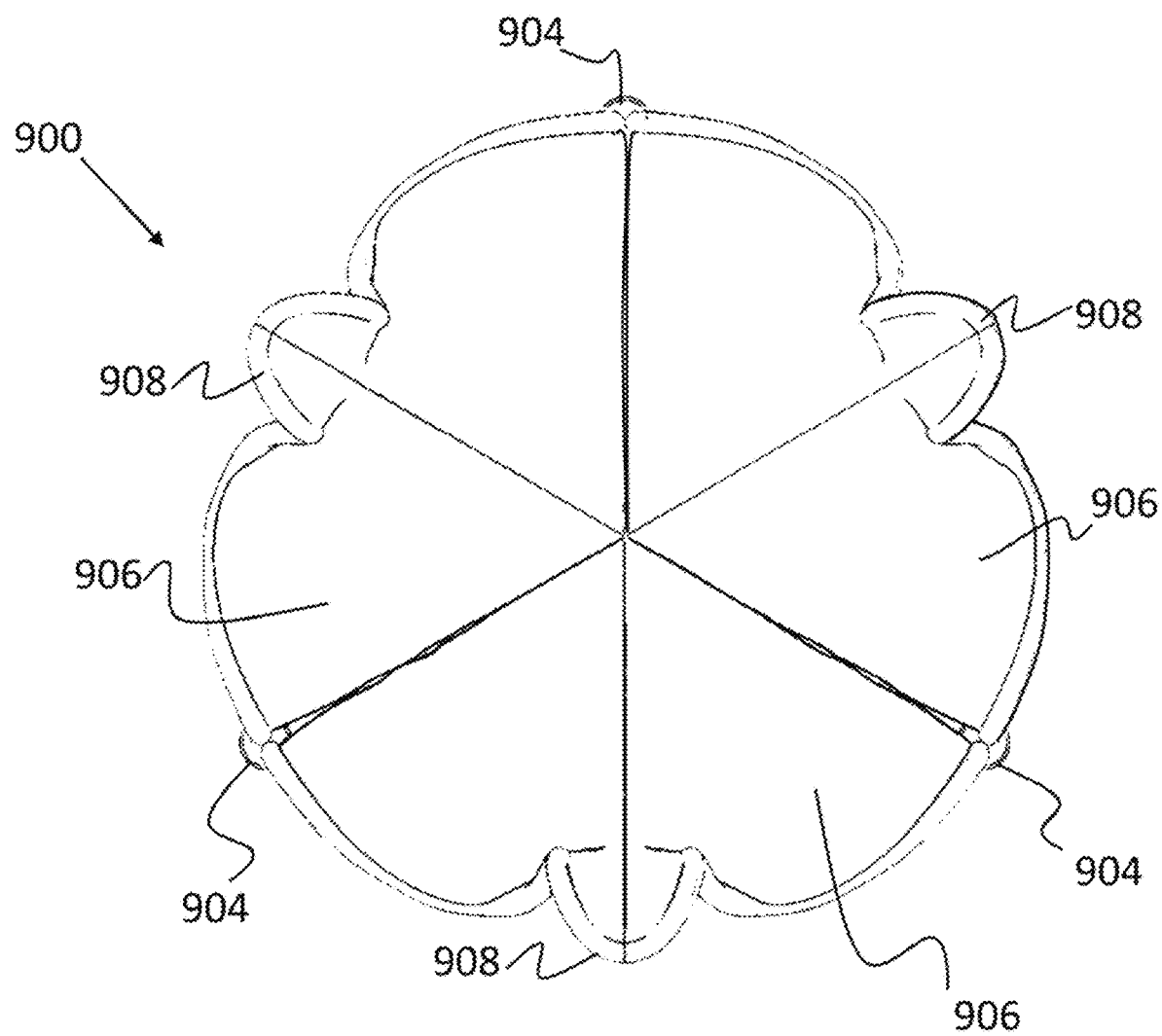
FIG. 9C is a bottom-view illustration of the collapsible atrioventricular valve prosthesis according to the principles of the present invention.
Figure 9D:
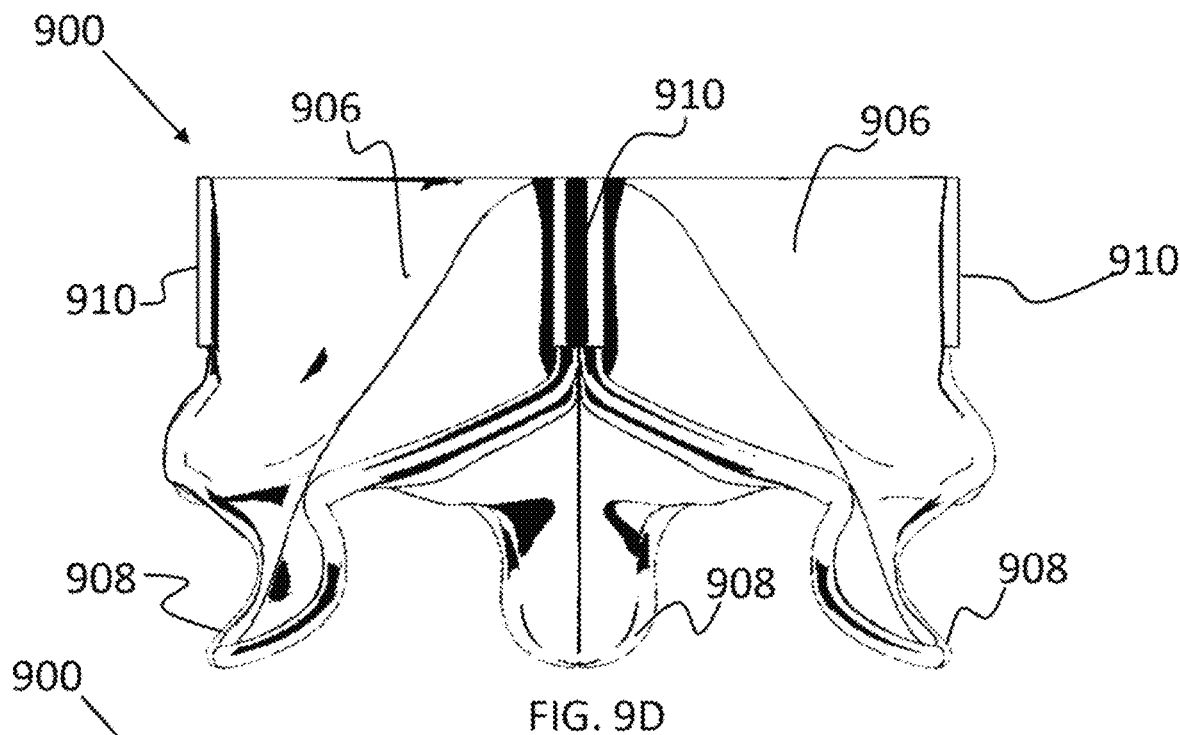
FIG. 9D is a front-view illustration of the collapsible atrioventricular valve prosthesis according to the principles of the present invention.
Figure 9E:
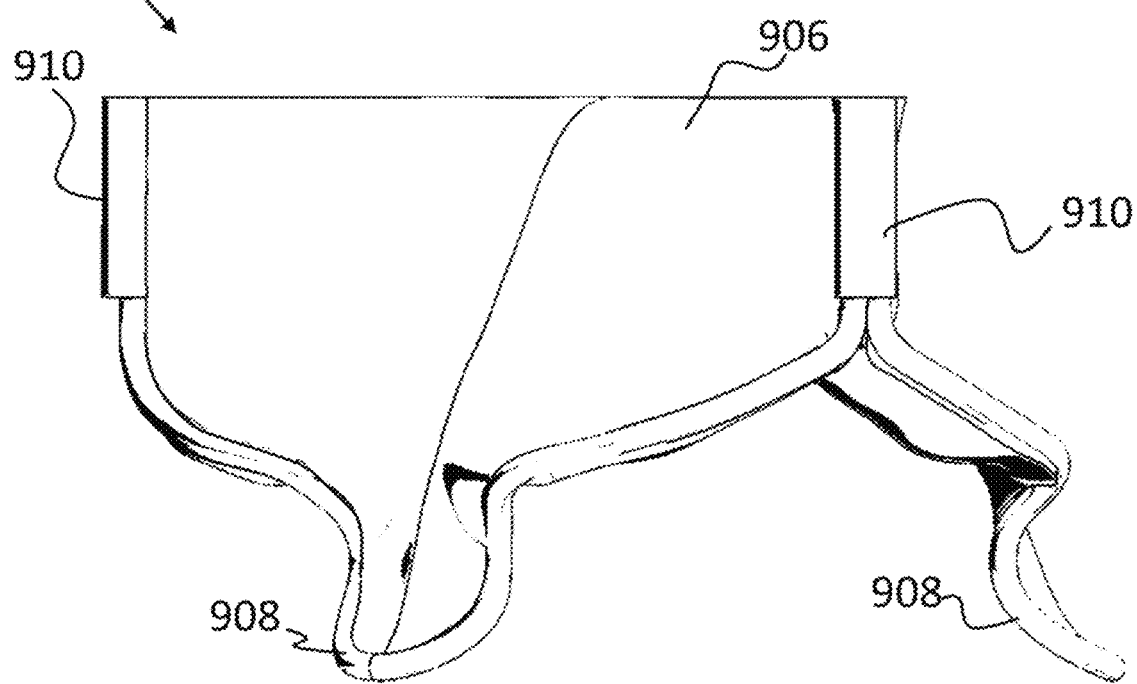
FIG. 9E is a side-view illustration of the collapsible atrioventricular valve prosthesis according to the principles of the present invention.

For example and as shown in FIGS. 9D and 9E, when the prongs 904 protrude upward, the catches 908 protrude in a generally downward direction. Or stated in the alternative, when the prongs 904 protrude downward, the catches 908 protrude in an upward direction.

As noted above, the leaflets 906 are formed of any suitable material, non-limiting examples of which include pericardial tissue, polymeric material, and leaflet tissue material. Further, the frame 902 is formed of any desired material, a non-limiting example of which includes a shape-memory material such as but not limited to Nitinol, Cobalt-Chromium or polymers. The frame 902 can be a single annulus that is formed, bent or otherwise shaped into the annulus frame 902. In another aspect, the frame 902 can be formed of several individual frame subcomponents that are connected together to collectively form the annulus frame 902. For example, the aspect as depicted in FIGS. 9A through 9E is formed of three frame subcomponents. Each frame subcomponent includes a pair of prong subcomponents 903 that are connected with one another via a connector 910 to collectively form a prong 904. Thus, in this example, each frame subcomponent is a wire frame that includes a pair of prong subcomponents 903 and at least one catch 908 formed therebetween. The connector 910 is any suitable mechanism or device that is suitable for connecting adjacent frame members. As a non-limiting example, the connector 910 is a hypo tube that passes over the ends of the wire prong subcomponents 903 and is crimped to securely hold the prong subcomponents 903. As such and in this example, each prong 904 is comprised of two wires (i.e., prong subcomponents 903) constrained together by a hypo tube (i.e., the connector 910).

Figure 10:
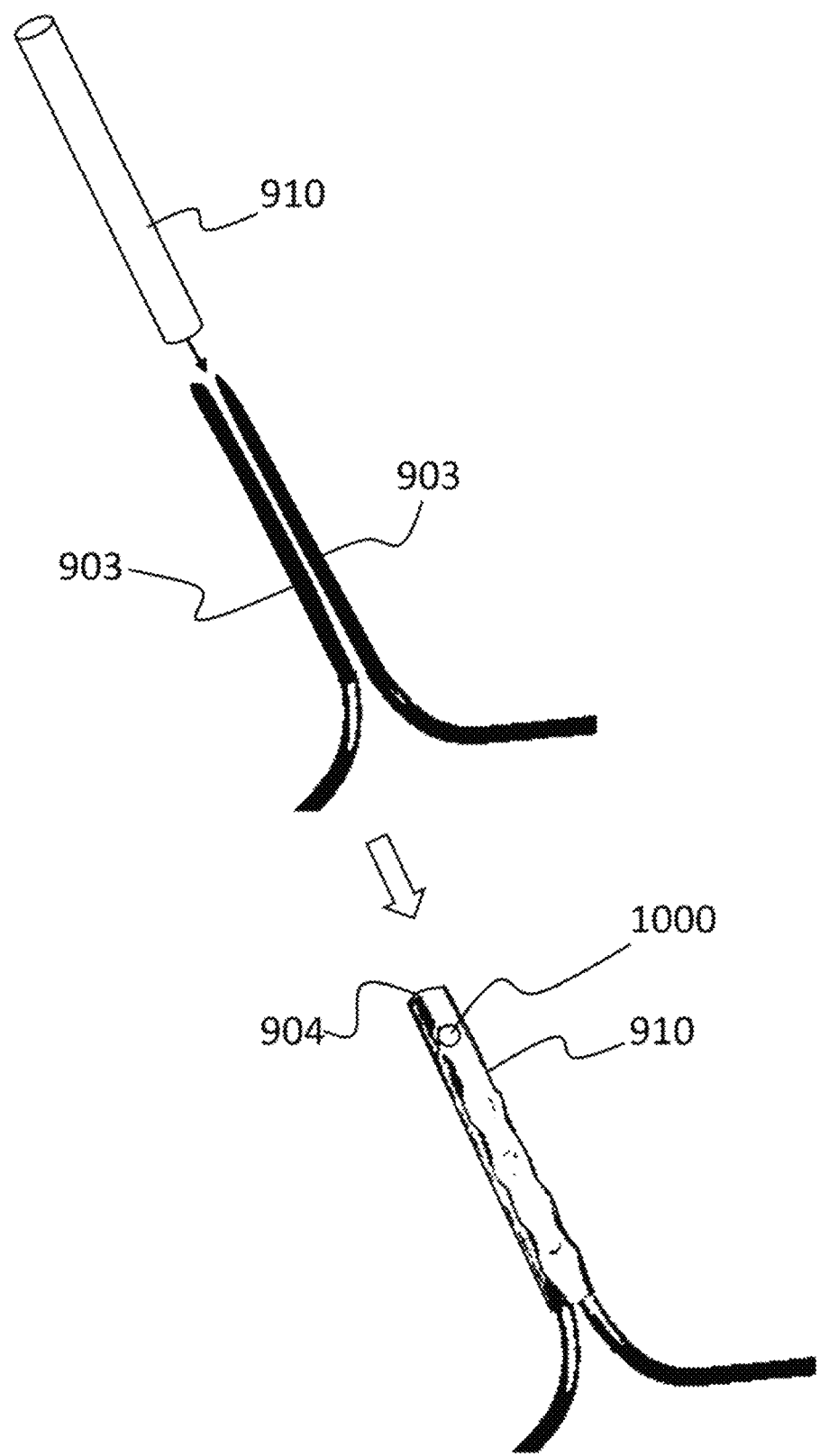
FIG. 10 is an illustration of a hypo tube connector for connecting adjacent prong subcomponents to collectively form a prong according to principles of the present invention.

An illustration of the hypo tube or connector 910 is shown in FIG. 10. In this example, the hypo tube or connector 910 is a stainless steel tube (or tube formed of any suitable material) that can be placed over adjacent wires (i.e., prong sub components 903) to collectively form the prong 904. In various embodiments, the hypo tube or connector 901 has a hole 1000 that can be used for attachment to the filaments or strings of a delivery system to assist in delivery of the collapsible atrioventricular valve.

In some aspects, the frame 902 is made of a monolithic wire (as depicted in FIG. 9A). In some aspects the frame 902 has a rough surface accommodating improved sitting at the atrioventricular junction. As can be appreciated by those skilled in the art, a rough surface is a surface that is not smooth. For example, a smooth surface is what one would find in a typical smooth wire (generally free from abrasions or bumps, etc.). Alternatively, a rough or roughened surface is what would result from a brief sanding of said wire. Further, in some aspects and as shown in FIG. 9A, the surface roughness is due to external components 920 added to the wire frame, such as added barbs, or other add-ons (e.g., wielded or glued on globules, etc.). It should be noted that although FIG. 9A depicts an example with just two external components 920 being added to the frame, any desired number of external components can be added at any desired location to assist in affixing the frame 902 with the heart or other atrioventricular location. In other aspects, the surface roughness is due to the inherent roughness of the wire frame 902 and can further be roughened due to sanding or other treatment to rough a surface.

As noted above, the collapsible atrioventricular valve 900 can be formed in a variety of shapes so long as there is at least one catch 908 between each prong 904. In various embodiments, the annulus frame is shaped as a saddle (as shown in FIG. 1A) or partially-saddle, provided that there is a catch 908 between each prong 904. Each added catch 908 provides an additional fixture or attachment that can be used to further strengthen the connection of the valve 900 with the patients surrounding tissue once installed. However, too many catches results in a configuration in which the catches 908 can become intertwined during deployment (when in the collapsed configuration) and prevent the valve 900 from expanding into the open configuration. Thus, it is desirable to form and position the catches 908 such that they are able to nestle, tuck, or rest against or proximate one another during the collapsed configuration (without becoming intertwined).

An example of a symmetric configuration having four catches 908 is shown in FIGS. 11A through 11D. Specifically, FIG. 11A is an isometric-view illustration of a frame 902 for the collapsible atrioventricular valve according to the principles of the present invention, in which there are two prongs 904 and four catches 908. FIGS. 11B through 11D depict the bottom-view, front-view, and side-views, respectively, of the frame 902. As clearly shown in FIG. 11B, the configuration as depicted include two catches 908 placed between each prong 904. Because there are only two prongs 904 and two catches 908 between each prong 904 (i.e., two sets of two catches 908), this configuration is referred to as 2:2. This configuration provides for an even number of catches 908 surrounding each prong 904 to evenly distribute the pressures of the valve in operation across the prongs 904.

Figure 12A:
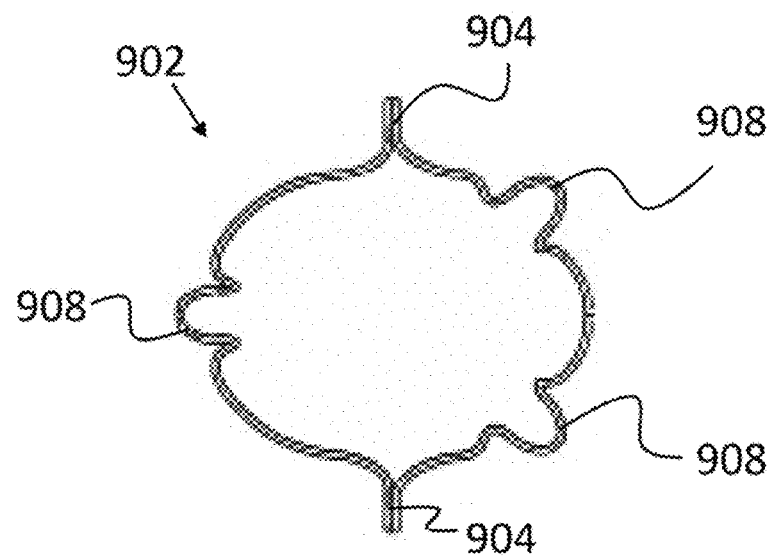
FIG. 12A is a bottom-view illustration of a frame according to the principles of the present invention.
Figure 12B:
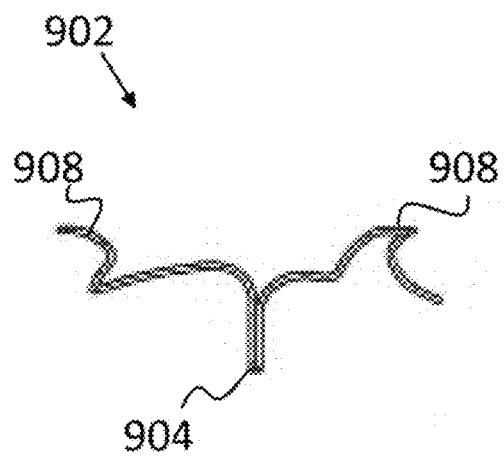
FIG. 12B is a front-view illustration of the frame depicted in FIG. 12A.
Figure 12C:
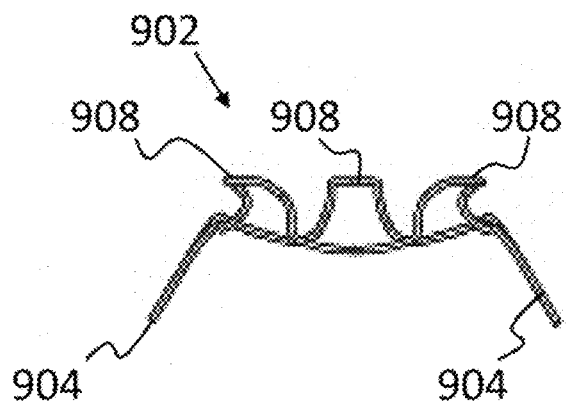
FIG. 12C is a side-view illustration of the frame depicted in FIG. 12A.

Another example of an asymmetric configuration of the frame 902 is shown in FIGS. 12A through 12C, which depict a bottom-view, front-view, and side-view, respectively, of the frame 902. In the example as depicted in FIGS. 12A through 12C, there are two prongs 904 and three catches 908. As clearly shown in FIG. 12A, the configuration as depicted include two catches 908 placed between the prongs 904 on one side of the frame 902, while there is only one catch 908 between the prongs 908 on the other side of the frame 902. Because there are two two catches 908 on one side while one catch 908 on the other side, this configuration is referred to as 2:1. This configuration provides for an uneven number of catches 908 around the frame 902 with respect to the prongs 904. Importantly, the addition of the additional catches 908 (such as the two catches 908) on one side provides a better anchor or anchoring of the valve 900 with the surrounding native tissue when installed in a patient. Also, it is desirable to form the frame 902 such that it does not have too many catches 908 that will increase the profile of the valve 900 and make it difficult to deliver. Further, pushing or otherwise constricting the left ventricular outflow track is not desirable as to do so could impede functioning of the aorta valve. Thus, the valve 900 in the configuration as shown in FIGS. 12A through 12C includes only a single catch 908 on one side to avoid overly anchoring against or otherwise constricting the left ventricular outflow track, while the other side of the valve 900 can optionally include more catches, such as the two catches 908 depicted in FIGS. 12A through 12C.

Figure 13:
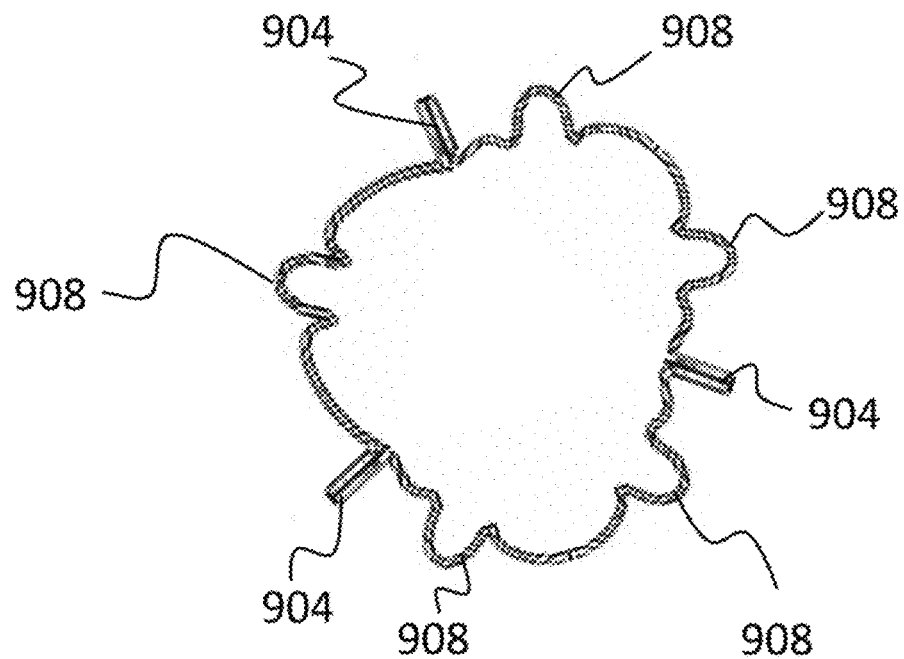
FIG. 13 is a bottom-view illustration of a frame of a collapsible atrioventricular valve according to the principles of the present invention.

Another example configuration of the frame 902 is shown in FIG. 13, which depicts a bottom-view of the frame 902. In the example as depicted in FIG. 13, there are three prongs 904 and five catches 908. As understood by those skilled in the art given the description above, the prongs 904 project in a direction that is generally opposite that of the catches 908, similar to the configuration as depicted in the front and side views as described above (e.g., see FIGS. 12B and 12C). In this aspect, the frame 902 includes two sets of two catches 908 placed between the prongs 904 on one side of the frame 902, while there is only one catch 908 between the prongs 904 on the other side of the frame 902. Because there is one catch 908 on one side of the frame 902 and two sets of two catches 908 on the other side, this configuration is referred to as 1:2:2. This configuration provides for an uneven number of catches 908 around the frame 902 with respect to the prongs 904. As noted above, an advantage to this is configuration is that it is a tri-cuspid valve (as opposed to the bi-cuspid valve of FIG. 12A) which is often more commercially desirable and can in many cases be more stable or less prone to failure. Notably, the 1:2:2 configuration allows for two sets of catches 908 to securely anchor the valve while installed, yet still includes a single catch 908 on one side to minimize the pushing or otherwise constriction of the left ventricular outflow track.

It should also be noted that the various frames 902 can be formed in any desired shape. For example, the profile views of FIGS. 12B and 12C show that the frame 902 between the catches 908 and prongs 904 has a desirable slight curvature. In other aspects, it should be noted that the frame 902 can be formed such that it is flat. For example, the catch 908, prong 904 and annulus frame are all flattened to spread out in a single plane. Or, in another aspect, the frame 902 is flat laterally such that profile views (such as those depicted FIGS. 12B and 12C, or other profile views of other configurations) would depict the frame 902 portion between the prongs 904 and catches 908 as being flat, with the prongs 904 projecting upward and the catches 908 projecting downward from the flattened frame 902 therebetween.

Figure 14:
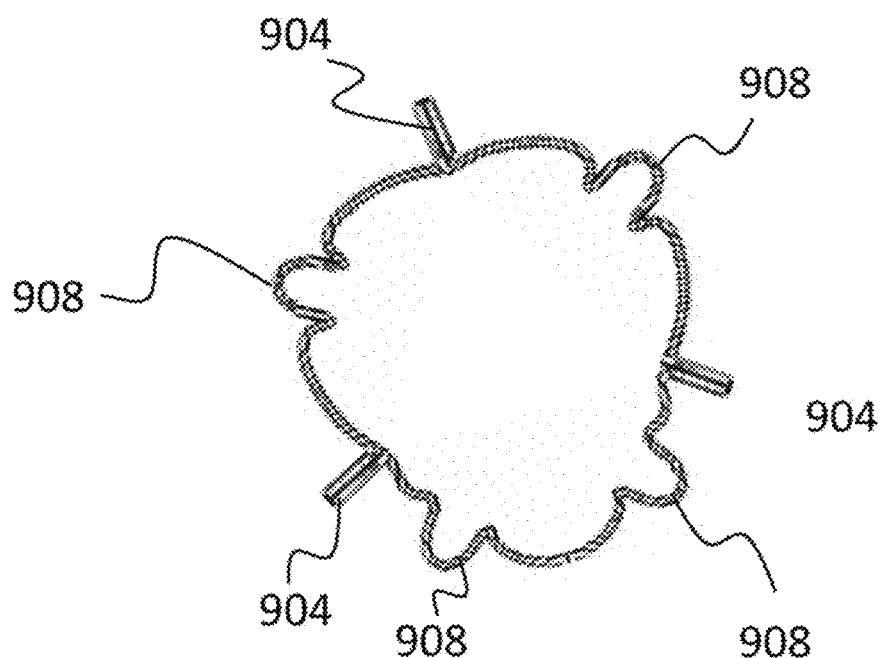
FIG. 14 is a bottom-view illustration of a frame of a collapsible atrioventricular valve according to the principles of the present invention.

Yet another example configuration of the frame 902 is shown in FIG. 14, which depicts a bottom-view of the frame 902. In the example as depicted in FIG. 14, there are three prongs 904 and four catches 908. As understood by those skilled in the art and as was the case above, the prongs 904 project in a direction that is generally opposite that of the catches 904, similar to the configuration as depicted in the front and side views as described above (e.g., see FIGS. 12B and 12C). In this aspect, the frame 902 includes one set of two catches 908 placed between the prongs 904 on one side of the frame 902, while there is only one catch 908 between each of the sets of prongs 904 on the other side of the frame 902. In other words, the configuration is such that there is one catch 908, one prong 904, one catch 908, one prong 904, two catches 908, and the last prong 904. As such, this configuration is referred to as 1:1:2. This configuration provides for an uneven number of catches 908 around the frame 902 with respect to the prongs 904. An advantage to the 1:1:2 configuration is that allows for at least one set of catches 908 between the prongs 908 to securely anchor the valve while installed, while further minimizing the profile of the frame 902 and the constrictive effects of the catches 908 on the surrounding tissue by having only single catch 908 between the remaining sets of prongs 904, thereby further minimizing the pushing or otherwise constriction of the left ventricular outflow track.

As noted above, the frame 902 can be formed in a variety of shapes. For example, FIGS. 9B, 11B, and 12A depict configurations in which a cross-section of the inflow is in a generally circular shape, whereas FIGS. 13 and 14 depict configurations in which the cross-section of the inflow is in a generally triangular shape.

Figure 15:
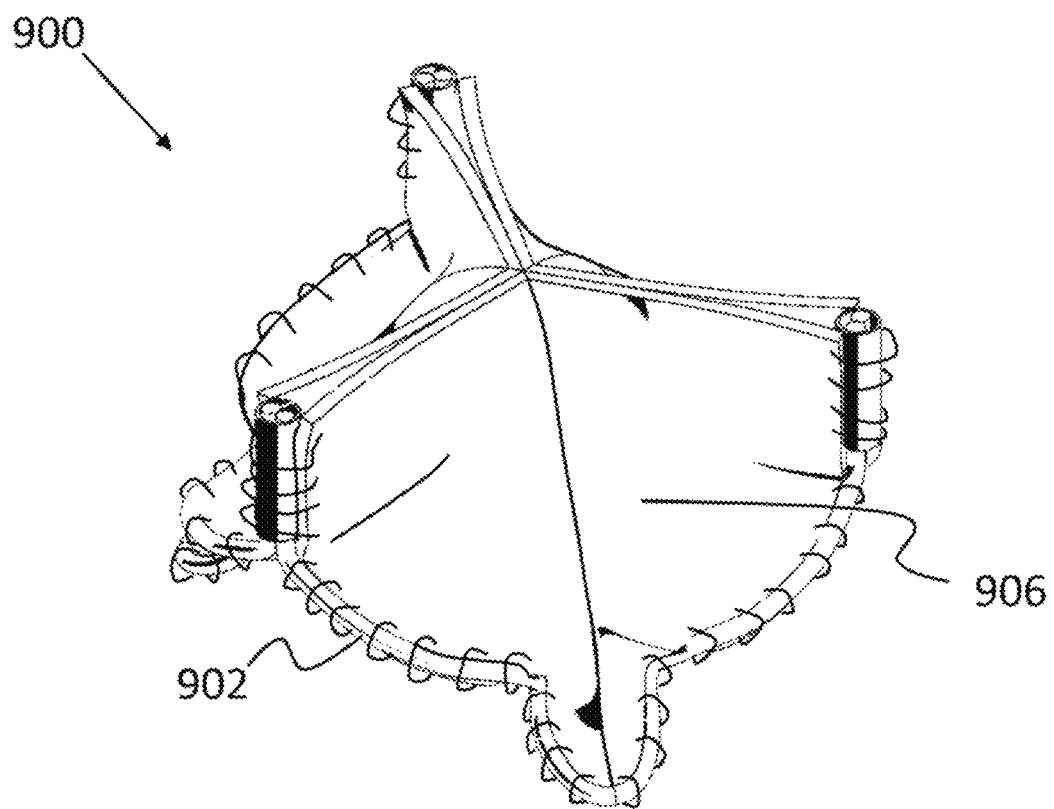
FIG. 15 is an isometric-view illustration of a collapsible atrioventricular valve prosthesis according to the principles of the present invention.

As noted above and as shown in FIG. 15, the leaflets 906 are affixed with the frame 902. The leaflets 906 are affixed with the frame using any suitable technique, process, or device. As a non-limiting example and as depicted in FIG. 15, the leaflets 906 are sewn or otherwise stitched to the frame 902 to form the collapsible atrioventricular valve 900.

Figure 16:
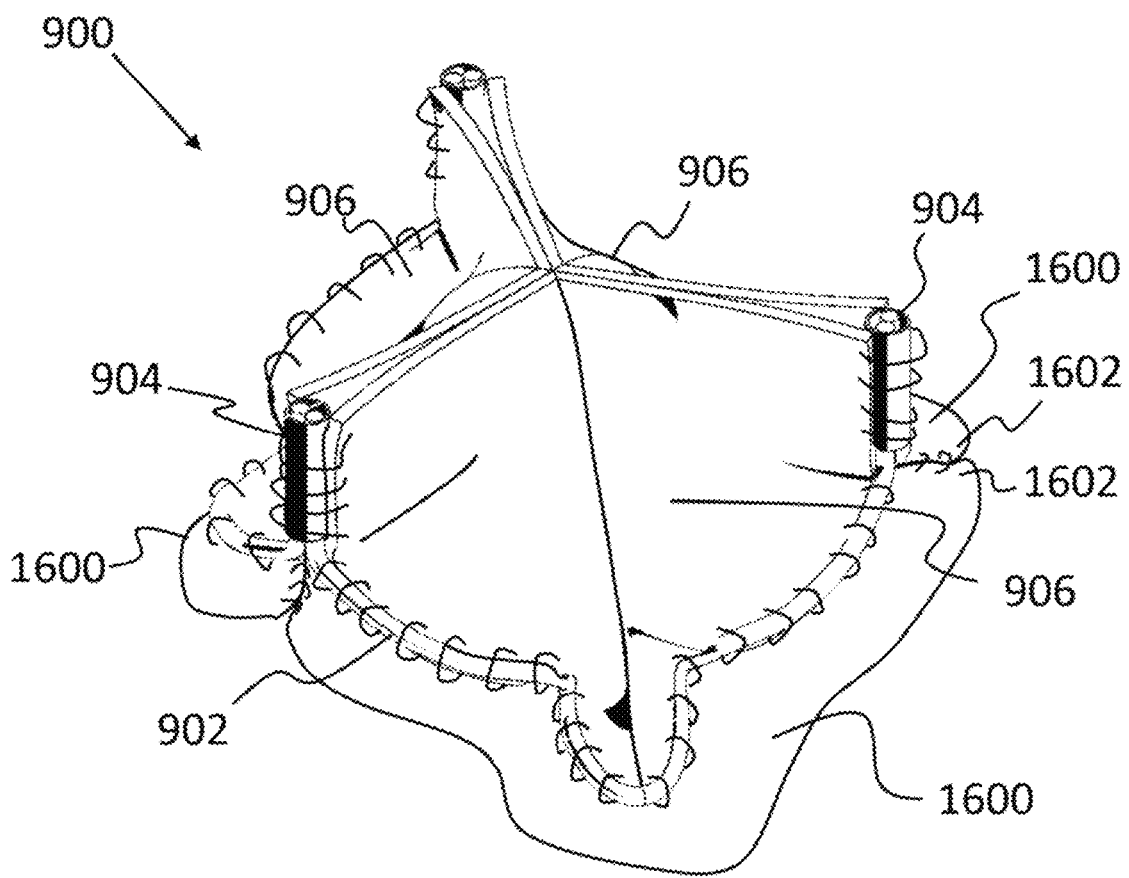
FIG. 16 is an isometric-view illustration of a collapsible atrioventricular valve prosthesis according to the principles of the present invention.

In some aspects and as shown in FIG. 16, a periphery skirt 1600 extends beyond the frame 902 and is attached to the valve's 900 circumference. The periphery skirt 1600 can be separately formed and attached with the frame 902 or, desirably, be formed as an extension of the leaflets 906. As a non-limiting example, the leaflets 906 are formed of a material (e.g., pericardial tissue, polymeric material, and leaflet tissue material, etc.) of sufficient size such that when the leaflets 906 are positioned underneath and against the frame 902 (as shown in FIG. 16), the material extends between adjacent prongs 904 and the frame 902, with additional material extending beyond the annulus frame 902. The leaflets 906 can then be affixed (e.g., sewn, etc.) with the frame 902 and prongs 904. In this non-limiting example, the material extending beyond the annulus frame 902 comprises the skirt 1600. The laterally peripheral edge 1602 of each periphery skirt 1600 can be affixed (e.g., sewn, glued, etc.) with the laterally peripheral edge 1602 of an adjacent periphery skirt 1600 to ensure that the periphery skirt 1600 flows completely around a circumference of the bottom portion of the valve 900. The periphery skirt 1600 serves to prevent or minimize paravalvular leakage.

Figure 17:
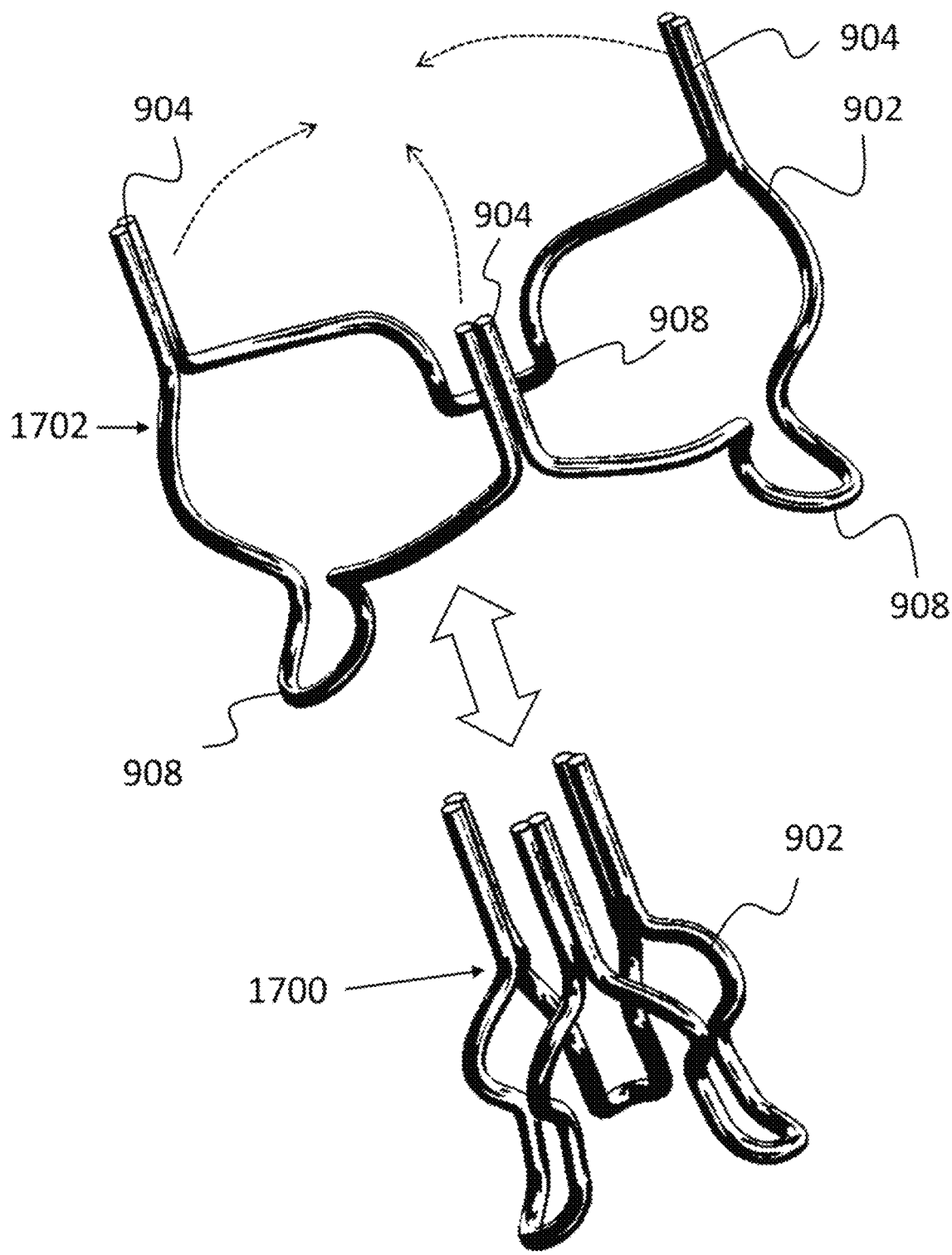
FIG. 17 is an isometric-view illustration of a frame of a collapsible atrioventricular valve prosthesis according to the principles of the present invention, depicting the frame in both collapsed and open configurations.
Figure 18:
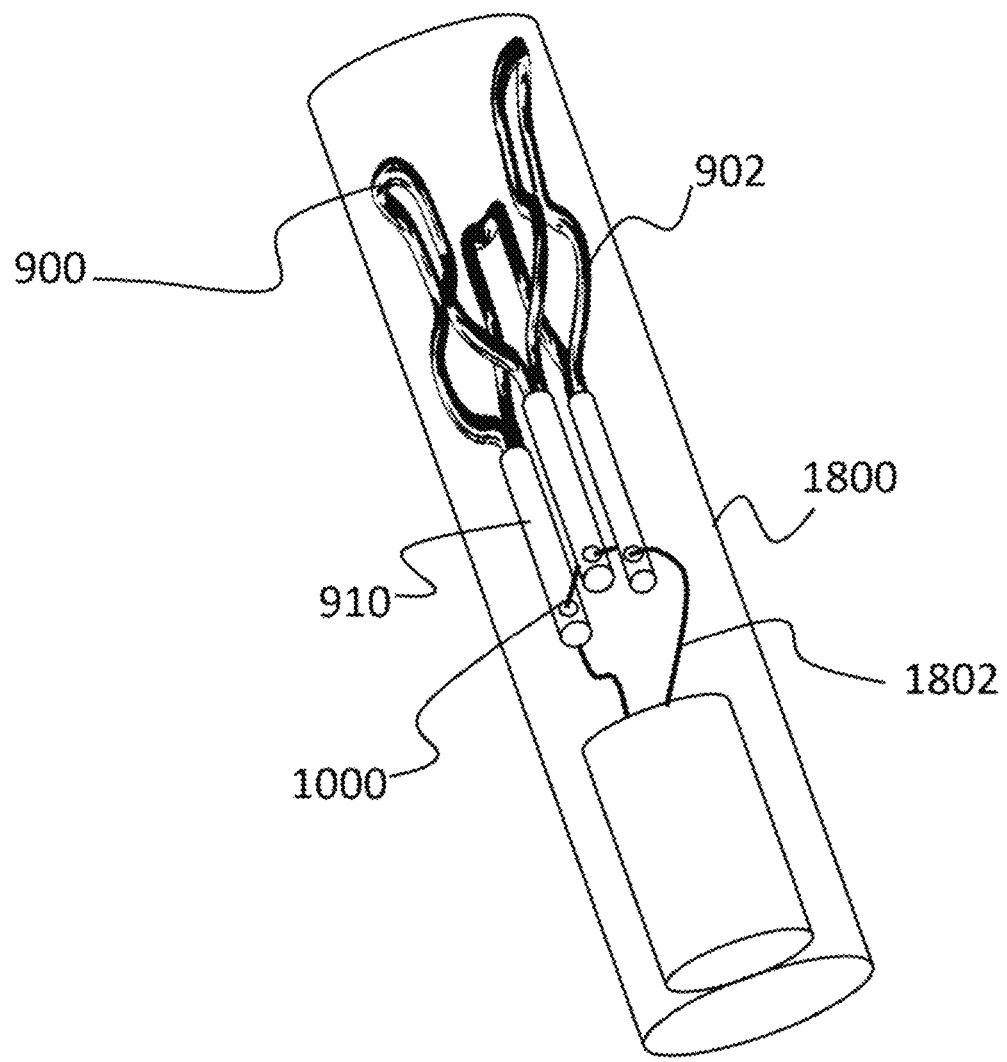
FIG. 18 is an illustration of a delivery system according to the principles of the present invention.

As noted above, the valve 900 is collapsible so that it can be collapsed into a delivery system for percutaneous heart valve delivery. For further understand and as shown in FIG. 17, the frame 902 of the valve is configurable between a collapsed configuration 1700 and an open configuration 1702. The frame 902 is collapsed into the collapsed configuration 1700 by pressing the prongs 904 and/or catches 908 toward one another. The collapsed configuration 1700 allows the valve to be delivered into position against a native atrioventricular valve annulus and upon expanding to the open configuration 1702, the atrioventricular valve is secured in place by the catches 908 (i.e., appendices or fixtures). For example, FIG. 18 depicts the valve 900 in a collapsed configuration and positioned with a delivery system 1800 for delivery to a desired site. Note that the leaflets are removed from the image for illustrative purposes to depict the frame 902 and its hypo tubes 910 and corresponding holes 1000 for connecting with the filaments 1802 of the delivery system 1800. It should be noted that any suitable delivery system 1800 can be employed with the valve 900 according to the principles of the present invention, a non-limiting example of which includes the delivery system as disclosed in U.S. Provisional Application No. 62/352,236, filed on Jun. 20, 2016, and entitled, "Delivery System For Percutaneous Delivery And Implantation Of Atrioventricular Heart Valves," the entirety of which is incorporated herein by reference as though fully set forth herein. Thus, in various embodiments, the valve is deliverable to the heart chambers via transapical approach. In other embodiments, the valve is deliverable to the heart chambers through peripheral vasculature, comprising but not limited to transfemoral artery/vein, aorta/vena cava, subclavian vasculature or jugular veins. Additionally, in various embodiments, the valve is deliverable to the heart chambers via surgical procedures, comprising but not limited to thoracotomy, mini-thoracotomy and minimally invasive heart surgery.

It should be understood that the specific examples and dimensions as described and illustrated are provided as non-limiting examples of suitable aspects; however, the invention is not intended to be limited thereto as it can be modified as needed and is to be accorded the widest scope consistent with the principles and novel features disclosed herein. Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A collapsible atrioventricular valve, comprising:
an annulus frame, wherein the annulus frame includes three prongs extending therefrom, with at least one catch positioned on the annulus frame between each of the three prongs, and wherein each prong is comprised of two wire-form structures constrained together by a hypo tube wrapped and permanently affixed around the two wire-form structures;
at least two leaflets attached with the annulus frame and prongs to form a valve; and
wherein the annulus frame is a saddle-shaped annulus having a crest reflecting curvature of the saddle-shaped annulus.

2. The collapsible atrioventricular valve as set forth in in claim 1, where the annulus frame further comprises at least one catch that acts to hold the annulus frame secure on an atrioventricular junction or at an atrial or ventricular side of a heart, the catch projecting from the annulus frame directly beneath the crest, whereby when implanted the collapsible atrioventricular valve lies between a heart's atrium and ventricle.

3. The collapsible atrioventricular valve as set forth in in claim 2, wherein the prongs project from the annulus frame in a first direction and the at least one catch projects from the annulus frame in a direction away from the first direction.

4. The collapsible atrioventricular valve as set forth in in claim 1, wherein the annulus frame is symmetric.

5. The collapsible atrioventricular valve as set forth in in claim 1, wherein the annulus frame is axisymmetric.

6. The collapsible atrioventricular valve as set forth in in claim 1, where the annulus frame is asymmetric.

7. The collapsible atrioventricular valve as set forth in claim 1, wherein the hypo tube has at least one hole that can be used for attachment to a delivery system.

8. The collapsible atrioventricular valve as set forth in in claim 1, wherein the valve is collapsible with a delivery system for percutaneous heart valve delivery.

9. The collapsible atrioventricular valve as set forth in in claim 1, wherein the annular frame is made of a monolithic wire.

10. The collapsible atrioventricular valve as set forth in in claim 1, wherein the annular frame is formed of a plurality of frame subcomponents.

11. The collapsible atrioventricular valve as set forth in in claim 1, wherein the annular frame is formed of shape-memory material selected from a group consisting of Nitinol, Cobalt-Chromium and polymers.

12. The collapsible atrioventricular valve as set forth in in claim 1, wherein the valve is configurable between a collapsed configuration and an open configuration, such the collapsed configuration allows the valve to be delivered into position against a native atrioventricular valve annulus and upon expanding to the open configuration, the atrioventricular valve is secured in place by the at least one catch.

13. The collapsible atrioventricular valve as set forth in in claim 1, wherein the leaflets are formed of a material selected from a group consisting of pericardial tissue, polymeric material, and leaflet tissue material.

14. The collapsible atrioventricular valve as set forth in in claim 1, wherein a surface of the annular frame is rough, thereby accommodating improved sitting at an atrioventricular junction.

15. The collapsible atrioventricular valve as set forth in in claim 14, wherein the annular frame is a wire frame and the surface of the annular frame is rough due to external components added to the wire frame.

16. The collapsible atrioventricular valve as set forth in in claim 14, wherein the annular frame is a wire frame and the surface of the annular frame is rough due to an inherent roughness of the wire frame.

17. The collapsible atrioventricular valve as set forth in in claim 1, further comprising a periphery skirt attached to a circumference of the annular frame, whereby the periphery skirt serves to minimize paravalvular leakage once implanted in a patient.

18. The collapsible atrioventricular valve as set forth in in claim 17, wherein the periphery skirt is formed of a material selected from a group consisting of pericardial tissue, polymeric material, and leaflet tissue material.

19. The collapsible atrioventricular valve as set forth in in claim 1, wherein the valve is collapsible and is deliverable to heart chambers via transapical approach.

20. The collapsible atrioventricular valve as set forth in in claim 1, wherein the valve is collapsible and is deliverable to heart chambers through peripheral vasculature, comprising transfemoral artery/vein, aorta/vena cava, subclavian vasculature or jugular veins.

21. The collapsible atrioventricular valve as set forth in in claim 1, wherein the valve is collapsible and is deliverable to heart chambers via surgical procedures comprising, thoracotomy, mini-thoracotomy and minimally invasive heart surgery.

22. The collapsible atrioventricular valve as set forth in in claim 1, wherein the annulus frame includes five catches, such that one catch is positioned on the annulus frame between a first set of adjacent prongs, and two catches are positioned on the annulus frame between a second set of adjacent prongs, and two catches are positioned on the annulus frame between a third set of adjacent prongs.

23. The collapsible atrioventricular valve as set forth in in claim 1, wherein the annulus frame includes four catches, such that one catch is positioned on the annulus frame between a first set of adjacent prongs, and one catch is positioned on the annulus frame between a second set of adjacent prongs, and two catches are positioned on the annulus frame between a third set of adjacent prongs.

* * * * *